(12) United States Patent
Zhang et al.

(10) Patent No.: US 9,751,866 B2
(45) Date of Patent: Sep. 5, 2017

(54) HEMI-AMINAL ETHERS AND THIOETHERS OF N-ALKENYL CYCLIC COMPOUNDS

(71) Applicant: ISP INVESTMENTS INC., Wilmington, DE (US)

(72) Inventors: Yi Zhang, Nutley, NJ (US); Osama M. Musa, Kinnelon, NJ (US)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 14/762,220

(22) PCT Filed: Jan. 21, 2014

(86) PCT No.: PCT/US2014/012254
§ 371 (c)(1),
(2) Date: Jul. 21, 2015

(87) PCT Pub. No.: WO2014/116560
PCT Pub. Date: Jul. 31, 2014

(65) Prior Publication Data
US 2015/0344461 A1 Dec. 3, 2015

Related U.S. Application Data

(60) Provisional application No. 61/755,225, filed on Jan. 22, 2013.

(51) Int. Cl.
*C07D 403/12* (2006.01)
*C07D 207/27* (2006.01)
(Continued)

(52) U.S. Cl.
CPC ......... *C07D 403/12* (2013.01); *C07D 207/27* (2013.01); *C07D 223/10* (2013.01); *C07D 233/34* (2013.01); *C07D 265/32* (2013.01); *C08B 11/02* (2013.01); *C08B 11/08* (2013.01); *C08B 11/12* (2013.01); *C08B 11/14* (2013.01); *C08B 11/193* (2013.01); *C08B 11/20* (2013.01); *C08B 31/08* (2013.01); *C08B 33/04* (2013.01); *C08B 35/04* (2013.01); *C08B 37/003* (2013.01); *C08B 37/009* (2013.01); *C08B 37/0033* (2013.01); *C08B 37/0039* (2013.01); *C08B 37/0042* (2013.01); *C08B 37/0045* (2013.01); *C08B 37/0084* (2013.01); *C08B 37/0087* (2013.01); *C08B 37/0093* (2013.01); *C08B 37/0096* (2013.01); *C08F 26/10* (2013.01)

(58) Field of Classification Search
CPC .. C07D 207/27; C07D 223/10; C07D 233/34; C07D 265/32; C07D 403/12; C08B 11/02; C08B 11/08; C08B 11/12; C08B 11/14; C08B 11/193; C08B 11/20; C08B 31/08; C08B 33/04; C08B 35/04; C08B 37/003; C08B 37/0033; C08B 37/0039
USPC ........... 526/265, 263, 264; 536/31; 540/524, 540/525, 531; 544/171; 548/324.1, 524, 548/547, 551
See application file for complete search history.

(56) References Cited

U.S. PATENT DOCUMENTS 3,823,160 A * 7/1974 Smith .................. C07D 207/27
504/156
4,009,195 A * 2/1977 Leister ................ C07D 207/27
558/358

(Continued)

OTHER PUBLICATIONS

Robert V. Slone ("Methacrylic Ester Polymers", Encyclopedia of Polymer Science and Technology vol. 3, pp. 249-277. Published Online: Oct. 22, 2001, John Wiley & Sons, Inc.).*

(Continued)

*Primary Examiner* — Ling Choi
*Assistant Examiner* — Chun-Cheng Wang
(74) *Attorney, Agent, or Firm* — Thompson Hine LLP; William J. Davis

(57) ABSTRACT

Described herein are hemi-aminal ethers and thioethers of N-alkenyl cyclic compounds that may be produced through a reaction comprising: (A) at least one first reactant represented by a structure (I), wherein X is a functionalized or unfunctionalized $C_1$-$C_5$ alkylene group optionally having one or more heteroatoms, and each $R_1$, $R_2$, and $R_3$ is independently selected from the group consisting of hydrogen and functionalized and unfunctionalized alkyl groups optionally having one or more heteroatoms, and (B) at least one second reactant having at least one hydroxyl moiety or thiol moiety. The hemi-aminal ethers and thioethers of N-alkenyl cyclic compounds may comprise a polymerizable moiety, in which case they may be left as-is or used to create homopolymers or non-homopolymers, or they may not comprise a polymerizable moiety. A wide variety of formulations may be created using the hemi-aminal ethers and thioethers of N-alkenyl cyclic compounds, including personal care, oilfield, and construction formulations.

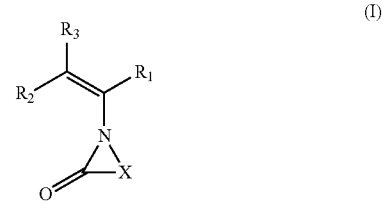

(I)

2 Claims, No Drawings

(51) Int. Cl.
| | |
|---|---|
| *C08F 26/10* | (2006.01) |
| *C07D 265/32* | (2006.01) |
| *C08B 11/14* | (2006.01) |
| *C07D 223/10* | (2006.01) |
| *C07D 233/34* | (2006.01) |
| *C08B 11/02* | (2006.01) |
| *C08B 11/08* | (2006.01) |
| *C08B 11/12* | (2006.01) |
| *C08B 11/193* | (2006.01) |
| *C08B 11/20* | (2006.01) |
| *C08B 31/08* | (2006.01) |
| *C08B 33/04* | (2006.01) |
| *C08B 35/04* | (2006.01) |
| *C08B 37/08* | (2006.01) |
| *C08B 37/00* | (2006.01) |

(56) References Cited

U.S. PATENT DOCUMENTS 5,700,946 A    12/1997   Shimasaki et al.
6,284,863 B1    9/2001   Ohta et al.

OTHER PUBLICATIONS

International Search Report, PCT/US2014/012254 published on Jul. 31, 2014.

* cited by examiner

HEMI-AMINAL ETHERS AND THIOETHERS OF N-ALKENYL CYCLIC COMPOUNDS

BACKGROUND

Field of the Invention

The invention provides hemi-aminal ethers and thioethers of N-alkenyl cyclic compounds optionally having one or more polymerizable moieties. The invention further provides a wide variety of compositions comprising the novel hemi-aminal ethers and thioethers of N-alkenyl cyclic compounds.

Description of Related Art

Related to the invention are the following references: U.S. Pat. Nos. 3,136,766; 3,531,471; 3,853,910; 4,036,712; 4,221,789; 4,288,300; 4,334,097; 4,397,750; 5,385,948; 5,144,074; and 5,703,098. Also related are the national patents CN 2009/10152605; DE 2,113,338; JP 5,097,799; RU 2,017,732 and 2,063,136. Two articles by M. F. Shostakovskii, et al. published in *Zelinskii Institute of Organic Chemistry of the Academy of Sciences of the USSR* in 1959 and 1961 also are related, as they both mention N-(1-butoxy), N-(1-ethoxy), and N-(1-isopropoxy) derivatives of N-ethyl caprolactam.

The N-alkoxy derivatives of N-alkyl lactams that are disclosed in the aforementioned references are deficient in properties required for effective performance in various industrial applications such as exploration, drilling and production of oilfield chemicals, industrial specialties, performance specialties, fuels, lubricants, personal care and pharmaceutical specialties.

Accordingly, there is a need for hemi-aminal ethers and thioethers of N-alkenyl cyclic compounds that have better performance attributes and are suitable for various industrial applications.

SUMMARY

The invention provides hemi-aminal ethers and thioethers of N-alkenyl cyclic compounds having at least one lactam, morpholinone, or cyclic urea moiety, at least one hemi-aminal ether or thioether moiety, and optionally one or more polymerizable moieties.

In one aspect, the hemi-aminal ethers and thioethers of N-alkenyl cyclic compounds are synthesized by Markonvikov's addition reaction of at least one first reactant that is an N-alkenyl lactam, morpholinone, or cyclic urea with at least one reactant having at least one hydroxyl moiety and/or thiol moiety. The compound having at least one hydroxyl and/or thiol moiety may optionally comprise one or more polymerizable moieties. Particularly, the reactant having at least one hydroxyl moiety may be selected from the group consisting of alcohols, polyols, hydroxyl functional aromatic and heteroaromatic compounds, polyvinyl alcohols, polyether polyols, polyacetal polyethers, hydroxyl functional polyalkylene polyamines, hydroxyl functional polyetheramines, hydroxyl functional polyethylene imines, polysaccharides, and combinations thereof. Particularly, the reactant having at least one hydroxyl moiety and at least one polymerizable moiety may be selected from the group consisting of hydroxyalkyl(meth)acrylates and hydroxyalkyl(meth)acrylamides. For the case of compounds having more than one hydroxyl moiety and/or thiol moiety, some or all of the hydroxy moieties and/or thiol moieties may react by Markovnikov addition with the first reactant.

The hemi-aminal ethers and thioethers of N-alkenyl cyclic compounds comprising one or more polymerizable moieties may serve as starting materials for synthesizing other compounds. For example, they may be homopolymerized or non-homopolymerized to yield their respective polymers. Alternatively, such polymerizable compounds may be formulated or used as-is, and polymerized later, e.g., in situ post-polymerization. Hemi-aminal ethers and thioethers of N-alkenyl cyclic compounds comprising more than one polymerizable moiety may be useful in synthesis of crosslinked and/or crosslinkable compositions.

In another aspect, the invention provides a wide variety of compositions comprising the compounds, polymers and non-homopolymers described herein. Such compositions include, but are not limited to personal care (e.g., hair care, sun care, skin care, color cosmetic, and oral care), adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

DETAILED DESCRIPTION

As used herein, the following terms have the meanings set out below.

The term "each independently selected from the group consisting of" means when a group appears more than once in a structure, that group may be selected independently each time it appears.

The term "functionalized" refers to replacing one or more hydrogens with one or more non-hydrogen groups, for e.g., alkyl, alkoxy, cycloalkyl, alkenyl, cycloalkenyl, alkynyl, and/or aryl groups. Alkyl, alkenyl and/or alkynyl groups include $C_1$-$C_{60}$), more particularly $C_1$-$C_{36}$, and most particularly $C_1$-$C_{18}$ groups. Cycloalkyl groups include cyclopentane, cyclohexane, cycloheptane, and the like. Alkoxy groups include methoxy, ethoxy, n-propoxy, isopropoxy, and the like. Aryl groups include benzenes, naphthalenes (2 rings), anthracenes (3 rings), and the like.

The term "hydrocarbyl" refers to straight-chain and/or branched-chain groups comprising carbon and hydrogen atoms with optional heteroatom(s). Particularly, the hydrocarbyl group includes $C_1$-$C_{60}$, more particularly $C_1$-$C_{36}$, and most particularly $C_1$-$C_{18}$ alkyl and alkenyl groups optionally having one or more hetero atoms. The hydrocarbyl group may be mono-, di- or polyvalent.

The term "heteroatom" refers to oxygen, nitrogen, sulfur, silicon, and/or phosphorous. The heteroatom may be present as a part of one or more functional groups on the hydrocarbyl chain and/or as a part of the hydrocarbyl chain itself.

The term "halogen" refers to chloro, bromo, iodo and/or fluoro.

The term "residue of" refers to a fragment of a reactant that remains after a reaction with another reactant(s). The residue may be mono-, di- or polyvalent.

A monomer is a small molecule that chemically bonds during polymerization to one or more monomers of the same or different kind to form a polymer.

The term "polymer" refers to a large molecule (macromolecule) comprising repeating structural units polymerized from one or more monomers connected by covalent chemical bonds.

The term "polymerization" refers to methods for chemically reacting monomers to form polymer chains. The type of polymerization method may be selected from a wide variety of methods. Such methods include, but are not limited to, free radical polymerization, such as classical radical polymerization and controlled radical polymerization, Nitroxide Mediation Polymerization (NMP), Atom Transfer Radical Polymerization (ATRP), and Reversible Addition Fragmentation Chain-Transfer (RAFT).

The term "homopolymer" refers to a polymer comprising essentially one type of monomer. Homopolymers include polymers polymerized from one monomer that may be modified during or after polymerization, for example, by grafting, hydrolyzing, or end-capping. Homopolymers may be associated with solvent adducts.

The term "non-homopolymer" refers to a polymer obtained by polymerization of two or more different kinds of monomers. The definition includes essentially all polymers that are not homopolymers. Nonlimiting examples of non-homopolymers include copolymers, terpolymers, tetramers, and the like, wherein the non-homopolymer may be a random, block, or an alternating polymer.

The term "solvent adduct" refers to a solvent molecule that is bonded to a compound, such as a polymer, by one or more covalent bonds, ionic bonds, hydrogen bonds, coordinate covalent bonds, and/or Van der Waals forces of attraction.

The term "(meth)acrylates" refers to both acrylates and methacrylates. Similarly, the term "(meth)acrylamides" refers to both acrylamides and methacrylamides.

The term "personal care composition" and "cosmetics" refer to such illustrative non-limiting compositions as skin, sun, oil, hair, and preservative compositions, including those to alter the color, condition, or appearance of the skin. Potential personal care compositions include, but are not limited to, compositions for increased flexibility in styling, durable styling, increased humidity resistance for hair, skin, color cosmetics, water-proof/resistance, wear-resistance, and thermal protecting/enhancing compositions.

The term "performance chemicals composition" refers to any non-personal care composition. Performance chemicals compositions serve a broad spectrum of arts, and include non-limiting compositions such as: adhesives; agricultural, biocides, coatings, electronics, household-industrial-institutional (HI&I), inks, membranes, metal fluids, oilfield, paper, paints, plastics, printing, plasters, and wood-care compositions.

The term "oilfield compositions" refers to a composition that may be used as an anti-agglomerant, emulsifier, de-emulsifier, gas hydrate inhibitor, kinetic hydrate inhibitor, shale swelling inhibitor, drilling fluid, fracturing fluid, and/or scale inhibitor.

In a first aspect, the invention provides novel hemi-aminal ethers and thioethers of N-alkenyl cyclic compounds having the structure:

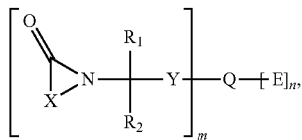

wherein each X is an independently selected functionalized or unfunctionalized alkylene group optionally having one or more heteroatoms such that the

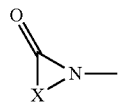

group is a 5- to 7-membered ring; each Y is independently selected from the group consisting of O and S; each $R_1$ and $R_2$ is independently selected from the group consisting of hydrogen and functionalized and unfunctionalized alkyl groups optionally having one or more heteroatoms, with the proviso that $R_1$ and $R_2$ attached to the same carbon are both not hydrogen at the same time; Q is a functionalized or unfunctionalized hydrocarbyl group optionally having one or more heteroatoms with the proviso that when m=1 and n=0, Q is a functionalized or unfunctionalized hydrocarbyl group having eight or more carbon atoms and optionally having one or more heteroatoms, and when m=2 and n=0, Q is a functionalized or unfunctionalized hydrocarbyl group having seven or more carbon atoms and optionally having one or more heteroatoms; each E is a polymerizable group; m is an integer equal to or greater than 1; and n is an integer equal to or greater than zero.

In particular embodiments, each $R_1$ and $R_2$ is independently selected from the group consisting of hydrogen and functionalized and unfunctionalized $C_1$-$C_8$ alkyl groups optionally having one or more heteroatoms, with the proviso that $R_1$ and $R_2$ attached to the same carbon are both not hydrogen at the same time. More particularly, each $R_1$ and $R_2$ is independently selected from the group consisting of hydrogen, methyl, and combinations thereof, with the proviso that $R_1$ and $R_2$ attached to the same carbon are both not hydrogen at the same time.

In particular embodiments, the hemi-aminal ethers and thioethers of N-alkenyl cyclic compounds may be obtained by Markovnikov electrophilic addition reaction of at least: (A) at least one first reactant represented by a structure

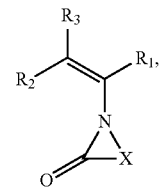

wherein X is a functionalized or unfunctionalized $C_1$-$C_5$ alkylene group optionally having one or more heteroatoms, and each $R_1$, $R_2$, and $R_3$ is independently selected from the group consisting of hydrogen and functionalized and unfunctionalized alkyl groups optionally having one or more heteroatoms, and (B) at least one second reactant having at least one hydroxyl moiety and/or thiol moiety. The reaction may be facilitated by acid catalysts, which are known to one skilled in the art. This catalyst may comprise one or more organic or inorganic acids, and non-limiting examples of suitable acid catalysts include sulfuric acid, hydrochloric acid, hydrobromic acid, hydroiodic acid, acetic acid, and trifluoroacetic acid. The addition level of the Markovnikov acid catalyst may be in the amounts typical to achieve electrophilic addition to a carbon-carbon double bond.

In particular embodiments, the first reactant may be selected from the group consisting of:

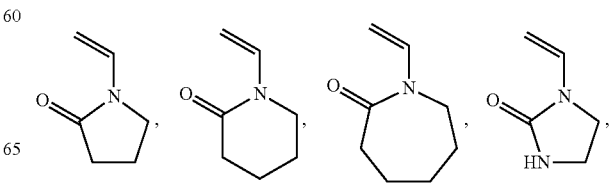

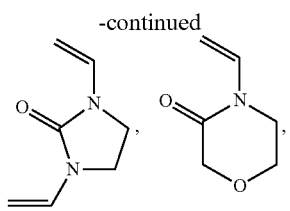

and combinations thereof. The N-vinyl cyclic urea may have vinyl substitution on one or both ring-nitrogen atoms.

In one embodiment, the second reactant having at least one hydroxyl moiety and/or thiol moiety does not comprise a polymerizable moiety. Particularly, the second compound may be selected from the group consisting of alcohols, polyols, hydroxyl functional aromatic and heteroaromatic compounds, polyvinyl alcohols, polyether polyols, polyacetal polyethers, hydroxyl functional polyalkylene polyamines, hydroxyl functional polyetheramines, hydroxyl functional polyethylene imines, polysaccharides, and combinations thereof.

Particularly, the alcohol may be selected from the group consisting of functionalized or unfunctionalized 2-ethyl-1-hexanol, 1-octanol, 1-nonanol, 1-decanol, 1-undecanol, 1-dodecanol, 1-tridecanol, 1-tetradecanol, 1-pentadecanol, 1-hexadecanol, 1-octadecanol, palmitoleyl alcohol, isostearyl alcohol, elaidyl alcohol, oleyl alcohol, linoleyl alcohol, elaidolinoleyl alcohol, linolenyl alcohol, elaidolinolenyl alcohol, ricinoleyl alcohol, nonadecyl alcohol, arachidyl alcohol, heneicosyl alcohol, behenyl alcohol, erucyl alcohol, lignoceryl alcohol, cholesterol, 2-(dibutylamino)ethanol, alcohol ethoxylates, and combinations thereof. More particularly, the alcohol may be selected from the group consisting of 2-ethyl-1-hexanol, 1-octanol, 1-dodecanol, 2-(dibutylamino)ethanol, $C_{12}$-$C_{13}$ alcohol ethoxylate, $C_{11}$ alcohol ethoxylate, and combinations thereof.

Non-limiting examples of alcohol ethoxylates include the following commercially available compounds from Stepan and combinations thereof: $C_{12}$-$C_{13}$ Alcohol Ethoxylate (BIO-SOFT® N23-3), $C_{11}$ Alcohol Ethoxylate (BIO-SOFT® N1-3), BIO-SOFT® EC-600, BIO-SOFT® EC-639, BIO-SOFT® EC-690, BIO-SOFT® N1-5, BIO-SOFT® N1-7, BIO-SOFT® N1-9, BIO-SOFT® N23-6.5, BIO-SOFT® N25-3, BIO-SOFT® N25-7, BIO-SOFT® N25-9, BIO-SOFT® N91-2.5, BIO-SOFT® N91-6, and BIO-SOFT® N91-8.

Particularly, the polyol may be selected from the group consisting of functionalized and unfunctionalized 2-butyl-2-ethyl-1,3-propanediol, 1,1,1-tris(hydroxymethyl)ethane, 1,1,1-tris(hydroxymethyl)propane, pentaerythritol, 2-bromo-2-nitro-1,3-propanediol, 3-bromo-1,2-propanediol, 3-chloro-1,2-propanediol, 2,2,3,3-tetrafluoro-1,4-butanediol, 1,4-dibromo-2,3-butanediol, tris(hydroxymethyl) nitromethane, 1,2-butanediol, 2,3-butanediol, 1,2,4-butanetriol, 2-hydroxymethyl-1,3-propanediol, threitol, 2,2,3,3,4,4-hexafluoro-1,5-pentanediol, 1,2-cyclopentanediol, 1,1-bis(hydroxymethyl)cyclopropane, 1,3-cyclopentanediol, 1,4-pentanediol, 1,5-pentanediol, 2,4-pentanediol, 2,2-dimethyl-1,3-propanediol, 3-methyl-1,3-butanediol, 1,2-cyclohexanediol, 1,3-cyclohexanediol, 1,4-cyclohexanediol, 1,3,5-cyclohexanetriol, 1,2-hexanediol, 1,5-hexanediol, 1,6-hexanediol, 2,5-hexanediol, hexylene glycol, 3-methyl-1,5-pentanediol, pinacol, 3,6-dithiaoctane-1,8-diol, 1,2,6-hexanetriol, glycerol, ethylene glycol, diethylene glycol, triethylene glycol, tetraethylene glycol, propylene glycol, dipropylene glycol, mannitol, sorbitol, and combinations thereof. More particularly, the polyol may be selected from the group consisting of 2-butyl-2-ethyl-1,3-propanediol, 1,1,1-tris(hydroxymethyl)ethane, and combinations thereof.

In particular embodiments, the invention provides novel N-alkenyl amide hemi-aminal ethers having a structure selected from the group consisting of:

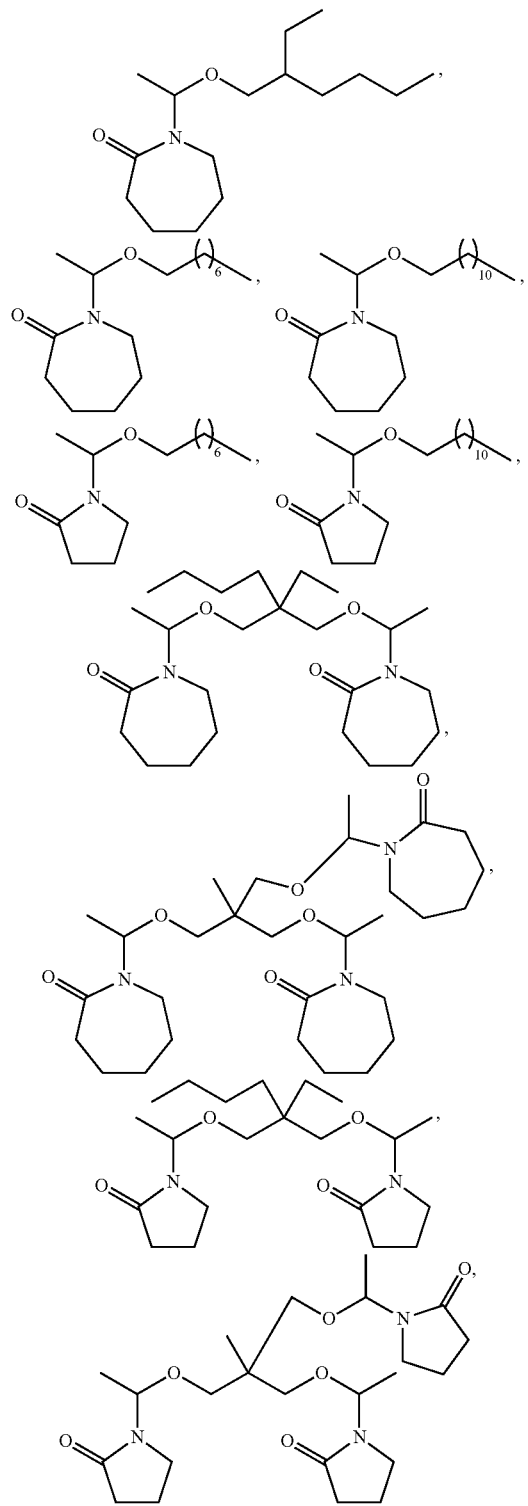

-continued

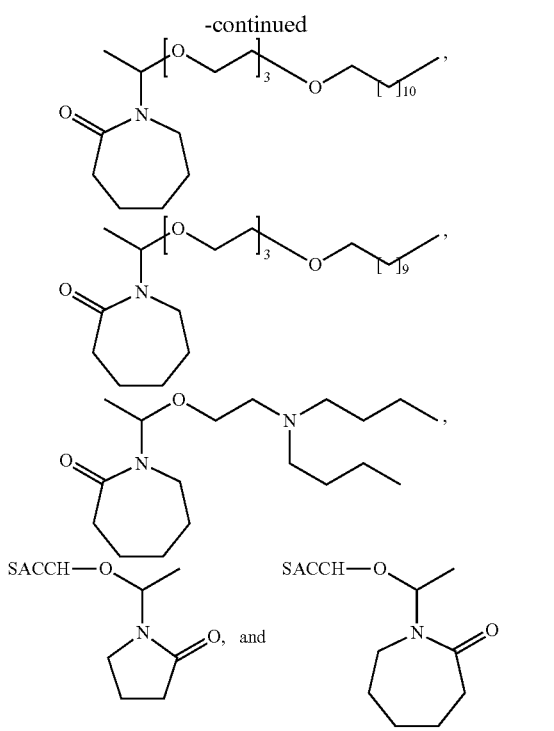

wherein the SACCH-O— is a residue of a polysaccharide.

Particularly, the polysaccharide may be selected from the group consisting of celluloses, starches, amylopectins, amyloses, chitins, chitosans, glucomannans, galactomannans, guar gums, locust bean gums, cassia gums, tara gums, fenugreek gums, mesquite gums, arabic gums, karaya gums, konjacs, pectins, xanthans, carrageenans, agar-agars, and alginates. More particularly, the cellulose may be selected from the group consisting of functionalized and unfunctionalized alkyl celluloses, hydroxyalkyl celluloses, alkylhydroxyalkyl celluloses, carboxyalkyl celluloses, alkylcarboxyalkyl celluloses, carboxyalkylhydroxyalkyl celluloses, alkylcarboxyalkyl hydroxyalkyl celluloses, and combinations thereof. Non-limiting examples of cellulose include functionalized and unfunctionalized methyl cellulose, ethyl cellulose, hydroxyethyl cellulose, hydroxypropyl cellulose, methyl hydroxyethyl cellulose, methyl hydroxypropyl cellulose, carboxymethyl cellulose, and combinations thereof.

In one embodiment, the second reactant having at least one hydroxyl moiety and/or thiol moiety further comprises a polymerizable moiety. Particularly, the polymerizable moiety may be selected from the group consisting of functionalized and unfunctionalized vinyls, allyls, (meth)acrylates, (meth)acrylamides, vinyl amides, vinyl esters, vinyl ethers, styrenes, maleic anhydrides, maleimides, maleates, fumarates, cinnamyls, vinyl imidazoles, vinyl triazoles, vinyl pyridines, vinyl sulfones, vinyl carbonates, vinyl carbamates, vinyl ureas, vinyl thiocarbamates, vinyl silanes, vinyl siloxanes, epoxides, oxetanes, benzoxazines, oxazolines and combinations thereof.

Particularly, the second reactant having at least one hydroxyl moiety and comprising a polymerizable moiety may be selected from the group consisting of functionalized and unfunctionalized hydroxyalkyl (meth)acrylates, hydroxyalkyl (meth)acrylamides and combinations thereof. Non-limiting examples of hydroxyalkyl (meth)acrylates include functionalized and unfunctionalized 2-hydroxyethyl acrylate, 2-hydroxyethyl methacrylate, 3-hydroxypropyl acrylate, 3-hydroxypropyl methacrylate, and combinations thereof. Non-limiting examples of hydroxyalkyl (meth)acrylamides include functionalized and unfunctionalized 2-hydroxyethyl acrylamide, 2-hydroxyethyl methacrylamide, 3-hydroxypropyl acrylamide, 3-hydroxypropyl methacrylamide, and combinations thereof.

In particular embodiments, the polymerizable N-alkenyl amide hemi-aminal ether has a structure selected from the group consisting of:

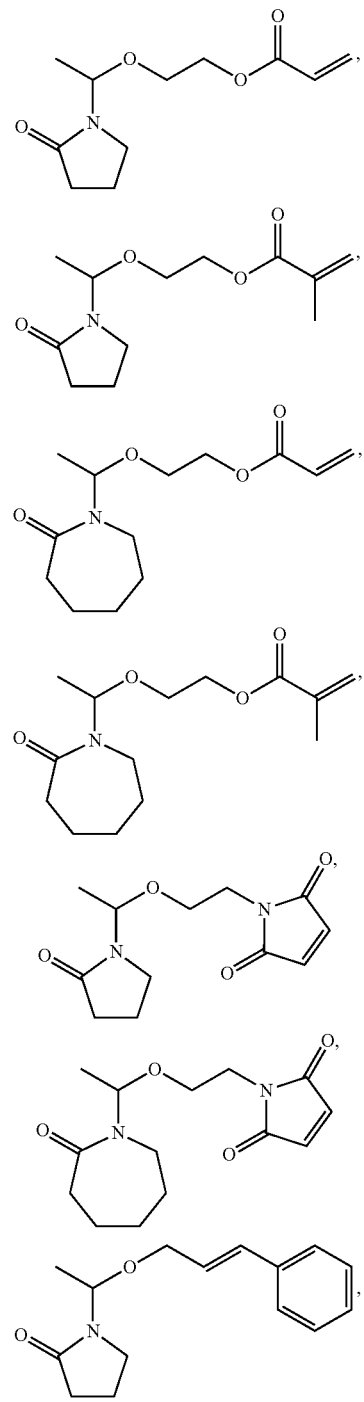

-continued

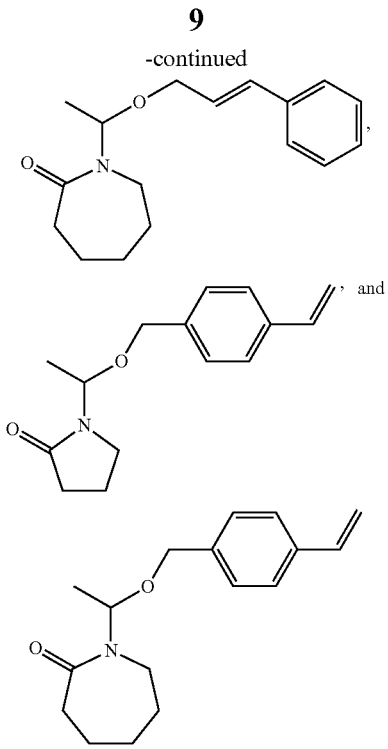

In a third aspect, the invention provides homopolymers obtained by polymerizing a monomer obtained by reaction of at least: (A) at least one first reactant represented by a structure

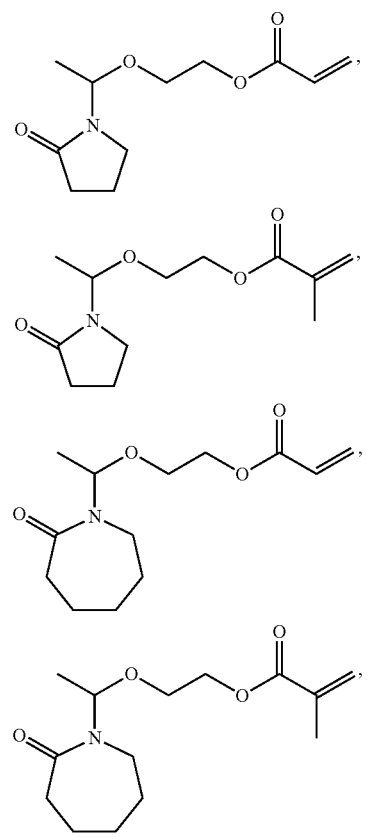

-continued

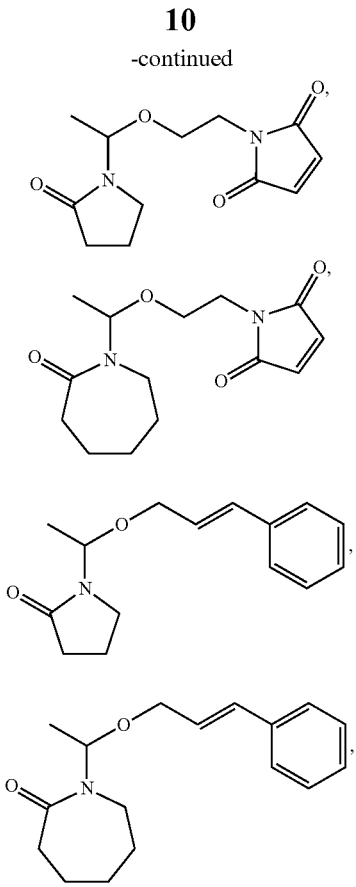

wherein X is a functionalized or unfunctionalized $C_1$-$C_5$ alkylene group optionally having one or more heteroatoms, and each $R_3$, $R_4$ and $R_5$ is independently selected from the group consisting of hydrogen and functionalized and unfunctionalized alkyl groups optionally having one or more heteroatoms, and (B) at least one second reactant having at least one hydroxyl moiety and/or thiol moiety and at least one polymerizable moiety.

In particular embodiments, the homopolymer is obtained by polymerizing a monomer selected from the group consisting of:

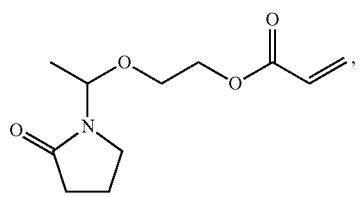

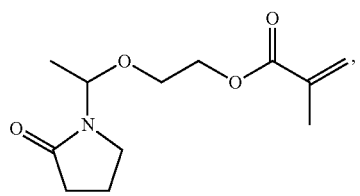

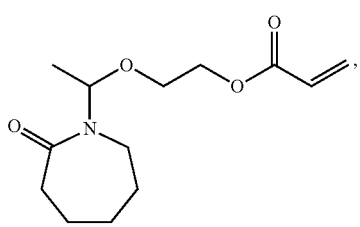

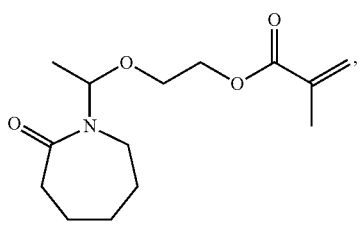

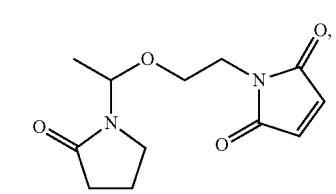

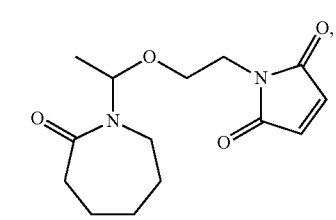

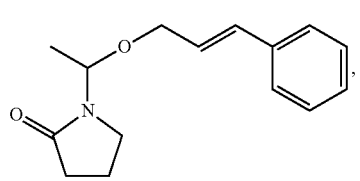

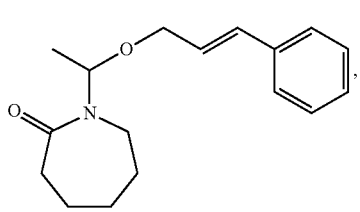

-continued

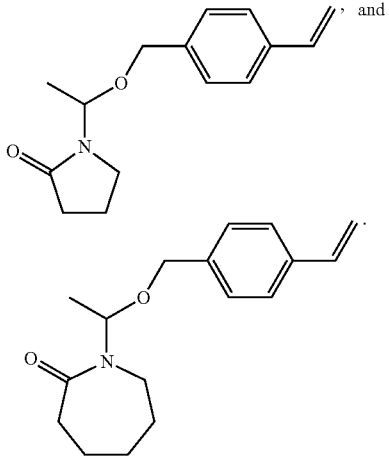

For example, the homopolymer may have a structure selected from the group consisting of:

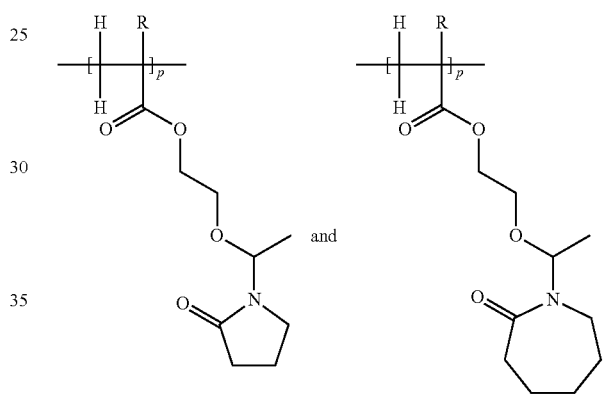

wherein R is hydrogen or methyl, and p is an integer ranging from 2 to about 10,000.

In a fourth aspect, the invention provides a non-homopolymer obtained by polymerizing: at least: (I) a first monomer obtained by reaction of at least: (A) at least one first reactant represented by a structure

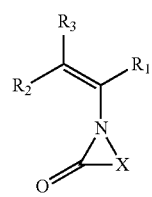

wherein X is a functionalized or unfunctionalized $C_1$-$C_5$ alkylene group optionally having one or more heteroatoms, and each $R_3$, $R_4$ and $R_5$ is independently selected from the group consisting of hydrogen and functionalized and unfunctionalized alkyl groups optionally having one or more heteroatoms, and (B) at least one second reactant having at least one hydroxyl moiety and/or thiol moiety and a polymerizable moiety, and (II) at least one second monomer different from the first monomer.

In particular embodiments, the first monomer has a structure selected from the group consisting of:

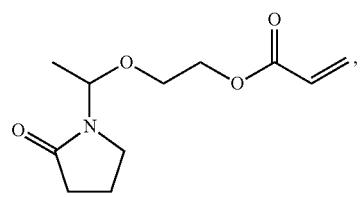
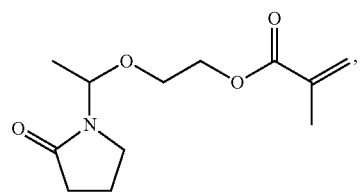
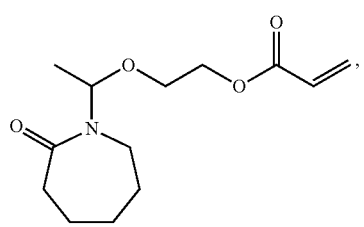
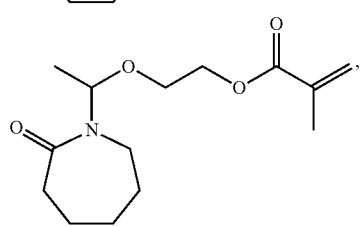
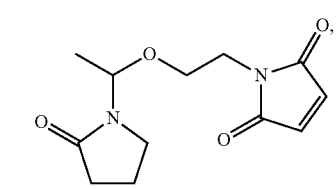
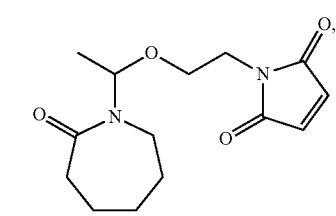
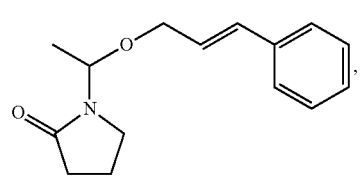
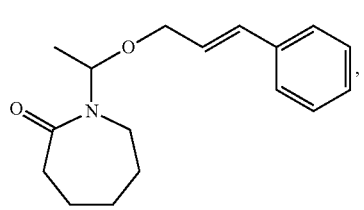

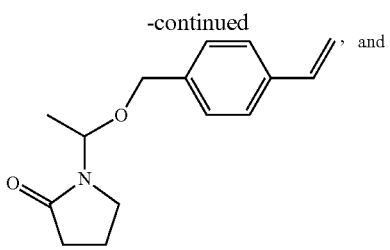
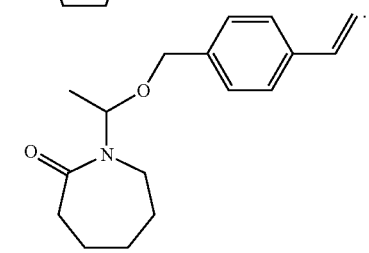

In particular embodiments, the second monomer may be selected from the group consisting of: polymerizable N-alkenyl amide hemi-aminal ethers different from the first monomer, functionalized and unfunctionalized 4-vinyl-1,2,3-triazoles, 5-vinyl-1,2,3-triazoles, (meth)acrylamides, (meth)acrylates, vinyls, allyls, maleic anhydrides, fumarates, maleates, maleimides, α,β-olefinically unsaturated carboxylic nitriles, styrenes, vinyl ethers, vinyl esters, vinyl acetates, vinyl amides, vinyl alcohols, vinyl carbonates, vinyl carbamates, vinyl thiocarbamates, vinyl ureas, vinyl halides, vinyl imidazoles, vinyl lactams, vinyl pyridines, vinyl silanes, vinyl siloxanes, vinyl sulfones, allyl ethers, benzoxazines, epoxides, oxazolines, oxetanes, and combinations thereof. More particularly, the second monomer may be selected from the group consisting of:

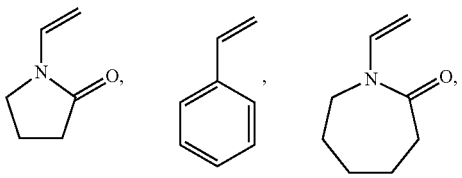
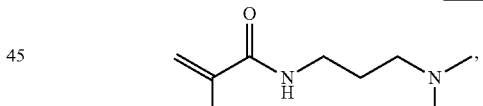
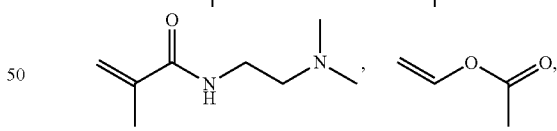
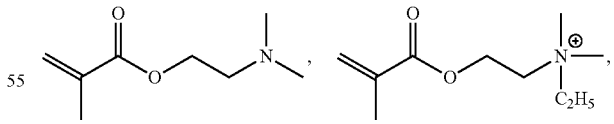
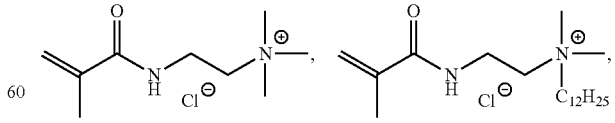
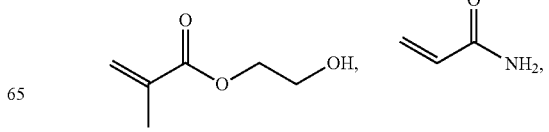

15

-continued

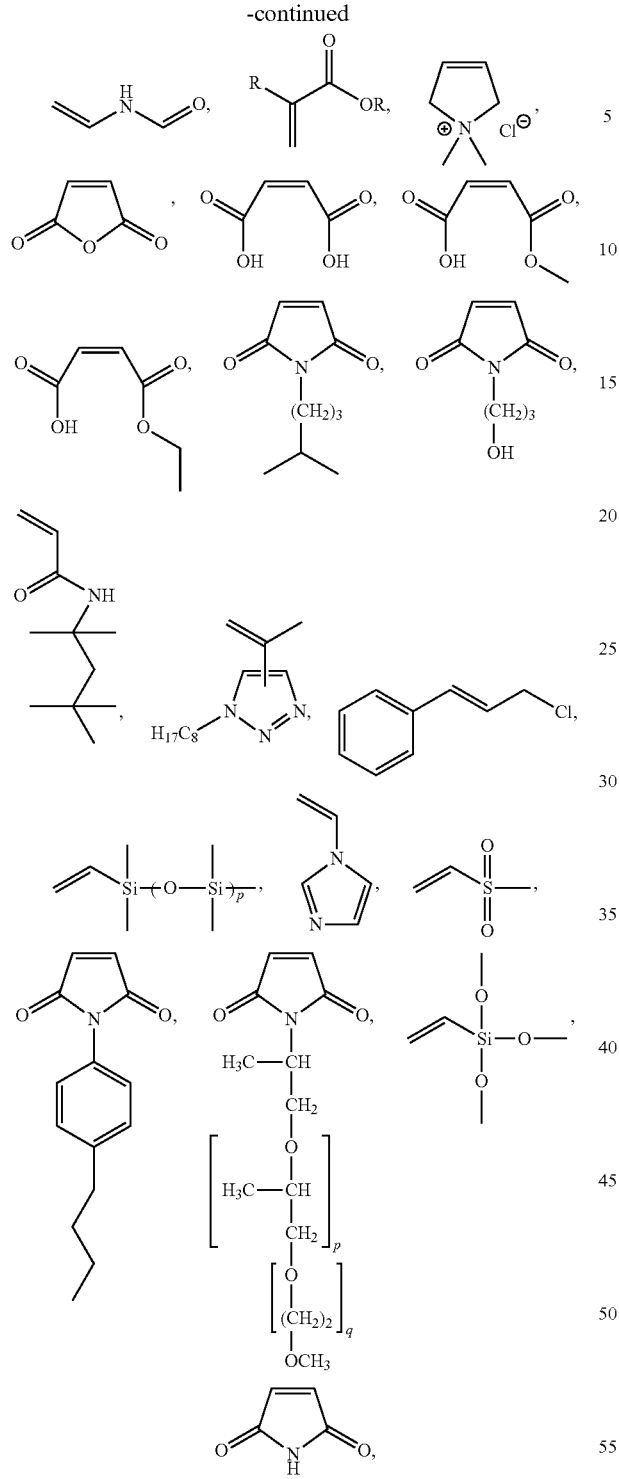

and combinations thereof, wherein each R is independently selected from the group consisting of hydrogen, and functionalized and unfunctionalized alkyl, cycloalkyl, alkenyl, aryl groups, and combinations thereof, wherein any of the before mentioned groups may be with or without heteroatoms, and p and q are independently selected integers equal to or greater than 1. Of course, the non-homopolymer may further comprise a third, fourth, or even more different types of monomers.

16

In particular embodiments, the non-homopolymer is obtained by polymerizing at least one first monomer having a structure selected from the group consisting of:

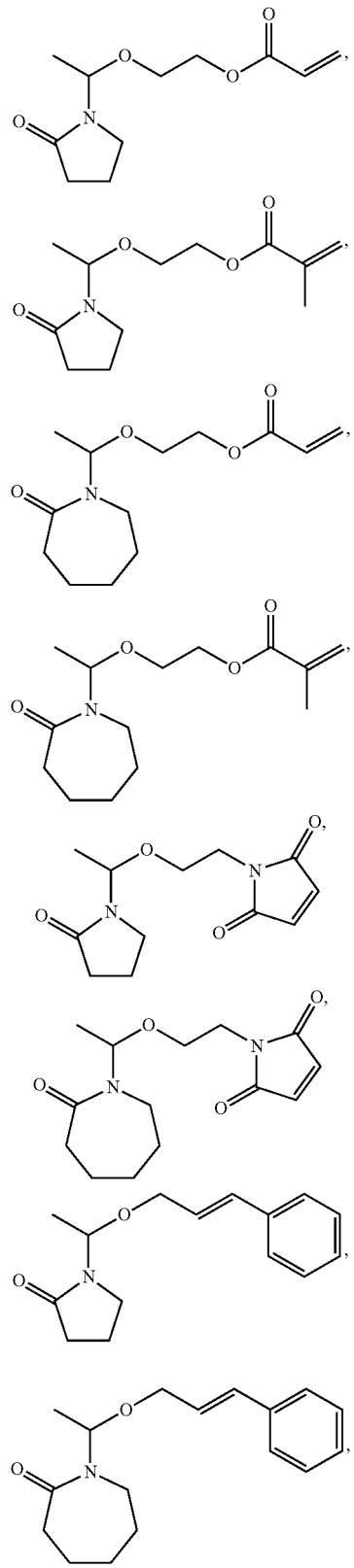

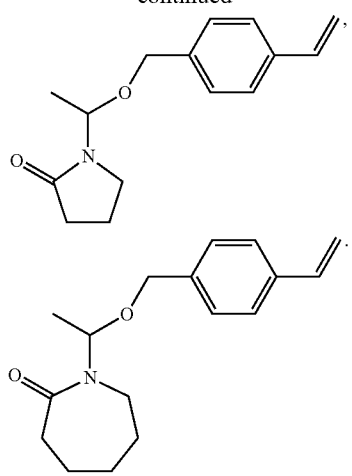

and combinations thereof; and at least one second monomer selected from the group consisting of functionalized and unfunctionalized N-vinyl caprolactam, N-vinyl pyrrolidinone and combinations thereof. One non-limiting example of such a non-homopolymer has a structure:

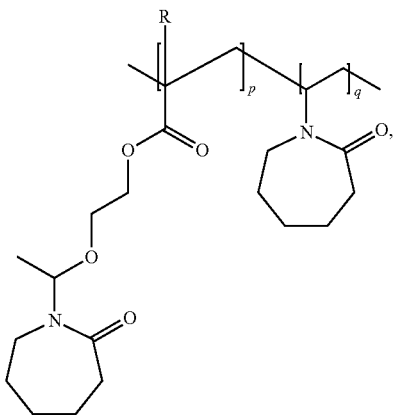

wherein R is hydrogen or methyl, and p and q are independently selected integers ranging from 2 to about 10,000. One skilled in the art can devise other non-homopolymers that fit within the scope of this invention.

The homopolymers and non-homopolymers according to the invention have a molecular weight ranging from about 5,000 to about 50,000,000 Da. More particularly, the polymers have a molecular weight ranging from about 10,000 to about 10,000,000 Da. Most particularly, the polymers have a molecular weight ranging from about 50,000 to about 1,000,000 Da.

In a fifth aspect, the invention provides a composition comprising an N-alkenyl hemi-aminal ether or thioether having the structure:

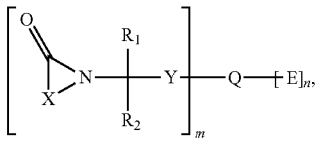

wherein X, Y, $R_1$, $R_2$, Q, E, m, and n are defined above.

In a sixth aspect, the invention provides compositions comprising a homopolymer obtained by polymerizing a monomer obtained by reaction of at least: (A) at least one first reactant represented by a structure

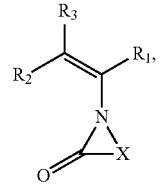

and (B) at least one second reactant having at least one hydroxyl moiety and/or thiol moiety and at least one polymerizable moiety, wherein X, $R_1$, $R_2$, and $R_3$ are defined above.

In a seventh aspect, the invention provides a composition comprising a non-homopolymer obtained by polymerizing: at least: (I) a first monomer obtained by reaction of at least: (A) at least one first reactant represented by a structure

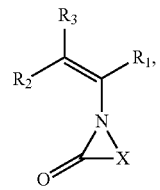

and (B) at least one second reactant having at least one hydroxyl moiety and/or thiol moiety and a polymerizable moiety, and (II) at least one second monomer different from the first monomer, wherein X, $R_1$, $R_2$, and $R_3$ are defined above.

The compositions according to the invention include, but are not limited to, personal care (e.g., hair care, sun care, skin care, color cosmetic, and oral care), adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions. For example, the composition may be an oilfield composition, such as an antiagglomerant, kinetic hydrate inhibitor, drilling fluid, fracturing fluid, or fluid-loss preventative composition.

The compounds, polymers, and non-homopolymers according to the invention may be used alone or in combination with other ingredient(s) in various compositions and product forms.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable that the compounds, homopolymers, non-homopolymers, and/or compositions of the invention (with or without any reaction solvent) be water dispersible and/or water soluble. In particular embodiments, the composition comprises a delivery solvent selected from the group consisting of 2-butoxyethanol, ethanol, ethylene glycol, poly(ethylene glycol), 1-propanol, 2-propanol, water, and blends thereof. The delivery solvent may comprise a hydroxyl group, e.g., an alcohol, a glycol ether, ethylene glycol, or a polar aprotic solvent, and/or blends thereof.

The compounds, homopolymers and/or non-homopolymers described herein may be used alone or in combination with other ingredient(s) in various compositions and product forms. Such compositions include, but are not limited to personal care compositions, adhesives, coatings, paints, electronics, Household, Industrial and Institutional (HI&I) compositions, inks, membranes, metal working fluids, oilfield chemicals, plastics and plasticizers, textiles, industrial products, biocides, pharmaceuticals/nutritionals, and agrochemical compositions.

The term "personal care composition" refers to a composition intended for use on or in the human body. Non-limiting, but specific types of personal care compositions include hair care compositions (encompassing styling and non-styling compositions), sun care compositions (encompassing after-sun compositions), skin care compositions, and oral care compositions.

Non-limiting applications of the hair care compositions include: hair styling, hair setting, hair sculpting, hair curling, hair holding, hair waving, hair fixing, hair maintaining, hair shaping, hair straightening, hair volumizing, hair relaxing, shampooing, hair conditioning, hair cleansing, promoting hair style durability, imparting humidity resistance to hair and hair styles, enhancing hair shine, repairing split ends of hair, enhancing hair manageability such as lightness, smoothness, softness, disentangling and/or suppleness of hair, modulating hair stylability, protecting hair from thermal damage, hair dyeing, hair coloring, hair bleaching, oxidation dyeing of hair, limiting hair color bleeding, protecting hair color, hair treating (e.g., anti-dandruff), anti-hair fall, and protecting hair from UV radiation.

The hair care compositions of the invention may be particularly used in hair styling. More particularly, the hair care compositions may be used to improve the hair stiffness, curl retention, and/or hair conditioning.

In particular embodiments, the hair care compositions may comprise the polymer(s) described herein in an amount from about 0.1% to about 50% by weight of the composition. More particularly, the polymer(s) may be present in an amount from about 0.5% to about 20% by weight, most particularly from about 1% to about 10% by weight of the composition.

The hair care compositions may further comprise one or more additional ingredients. Particularly, the additional ingredients may be selected from the group consisting of: skin care or hair care agents, hair styling agents, hair fixative agents, film formers, structurants, gelling agents, surfactants, thickeners, preservatives, viscosity modifiers, electrolytes, pH adjusting agents, perfumes, dyes, organosilicon compounds, anti-dandruff agents, anti-foaming agents, anti-frizz agents, penetrants, vitamins, conditioning agents, chelating agents, antimicrobial agents, preservatives, UV absorbers, sunscreens, natural extracts, propellants, carriers, diluents, solvents, pharmaceutical actives, lubricants, combing aids, plasticizers, solubilizers, neutralizing agents, vapor pressure suppressants, bleaching agents, hydrating agents, moisturizers, cosmetic adjuvants and/or additives, protectants, and mixtures thereof.

Non-limiting applications of the sun care compositions include: protecting skin and/or hair from UV radiation (including any or all of UV-A, UV-B and/or UV-C radiation), sun screening, skin anti-irritating, skin repairing, skin wrinkle masking, skin nourishing, skin moisturizing, skin relaxing, skin refreshing, skin cooling, skin soothing, skin tanning, skin tan prolonging, sun-less skin tanning, skin glowing, skin micro-glittering, skin shimmering, and skin anti-tanning.

Non-limiting applications of the skin care compositions include: protecting skin from UV radiation (including any or all of UV-A, UV-B and/or UV-C radiation), skin cleansing, face cleansing, body cleansing, insect repelling, antiperspirant, exfoliating skin, rejuvenating skin, influencing cell turnover, deodorant, astringent, imparting water resistance or water proofness to skin, decreasing and/or minimizing the appearance of skin wrinkles, decreasing and/or minimizing the appearance of skin blemishes (such as lentigo, skin discolorations, pimples, and/or acne), changing skin color (including skin lightening, skin brightening, skin color darkening, and color cosmetics for the face, cheeks, lips, eyelids, and/or eye lashes), skin iridescing, skin glossing, curling of eye lashes, eye lining, eye shadowing, mascara, removing facial and/or body hair, skin tightening, skin tanning, skin bronzing, skin blushing, prolonging skin tan, sun-less skin tanning, anti-tanning, skin antibacterial, skin anti-oxidant, skin anti-photoaging, skin anti-seborrheic, cell exchange and/or cell respiration activating of skin, skin conditioning, skin detoxifying, skin emollient, skin moisturizing, film forming on skin, skin healing-cicatrizing, skin immune-protecting, skin plumping, glossing, shading, plumping, and/or coloring of lips, skin revitalizing, skin energizing, skin re-sculpting, skin nourishing, skin smoothing, skin slimming, skin anti-irritating, and skin sanitizing.

Non-limiting applications of the oral care compositions include: tooth and/or mouth cleansing, providing denture adhesion, delivering and/or retaining actives to oral cavity, mouth washing, mouth refreshing, mouth rinsing, mouth gargling, providing oral hygiene, preventing, reducing, controlling, and/or removing tooth stain, preventing and/or controlling tooth decay, preventing and/or controlling tartar, tooth flossing, tooth whitening and/or bleaching, mouth treating, and tooth filling.

The polymers described herein also may be used alone or in combination with other ingredient(s) in pharmaceutical and/or nutritional compositions.

Non-limiting applications of the pharmaceutical and/or nutritional compositions include: providing anti-tack, binder, coating, disintegrating, dispersing, encapsulating, filling, film forming, lubricating, and solubilizing. Additional insight into how the polymers described herein find application in this art area may be found in the following publications by Ashland Specialty Ingredients: *Health and nutrition product guide-Performance enhancing products* (August 2008), *Plasdone™ povidones product overview* (April 2010), *Plasdone™ K-12 and K-17 povidones—Solubilizers for liquid softgel fill formulations* (September 2010), *Plasdone™ K-29/32 povidone—High efficiency binder for wet granulation* (April 2010), *Plasdone™ S-630 copovidone—Product Overview* (April 2010), *Polyplasdone™ Ultra and Ultra-10 crospovidones—Product overview* (September 2010), *Polyplasdone™ superdisintegrants—Product overview* (July 2010), *Polyplasdone™ crospovidone—Superdisintegrants for orally disintegrating and chewable tablets* (July 2010), *Polyplasdone™ crospovidone—Nonionic superdisintegrant for improved dissolution of cationic drugs* (July 2009), *Polyplasdone™ crospovidone—The solution for poorly soluble drugs* (July 2009), *Polyplasdone™ crospovidone—Novel pelletization aid for extrusion spheronization* (July 2010), *PVP-Iodine povidone iodine antiseptic agent* (March 2004), and *Pharmaceutical technical bulletin—PVP-Iodine for prophylaxis and treatment of*

*bovine mastitis* (December 2003). Each publication is hereby incorporated in its entirety by reference.

Any range in composition pH may be used. In embodiments wherein the composition is applied to keratinous material, the pH may range from about 2 to 12. pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, α-hydroxyacids, β-hydroxyacids, α,β-hydroxyacids, ω-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

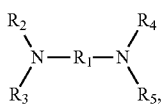

wherein $R_1$ is a propylene residue that may be optionally substituted with an hydroxyl group or a C1-C4 alkyl radical; $R_2$, $R_3$, $R_4$ and $R_5$ are identical or different and represent a hydrogen atom, a C1-C4 alkyl radical or C1-C4 hydroxyalkyl radical.

The composition also may comprise one or more buffers. Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate. The personal care compositions may be formulated in any of the product forms known to a person of ordinary skill in the art. Non-limiting product forms are described below.

Product Forms

Non-limiting hair care product forms include: shampoos, conditioners, aerosols, mousses, sprays, mists, gels, waxes, creams, lotions, glues, pomades, spritzes, solutions, oils, liquids, solids, W/O emulsions, O/W emulsions, suspensions, multiple emulsions, microemulsions, microencapsulated products, sticks, balms, tonics, pastes, reconstitutable products, nanoemulsions, solid lipid nanoparticles, liposomes, cubosomes, neosomes, putties, lacquers, serums, perms, volumizers, packs, flakes, 2-in-1 shampoo/conditioner products, and 3-in-1 shampoo/conditioner/styling products.

The compositions according to the invention may also take the form of after-shampoo compositions, to be rinsed off or not, for permanents, straightening, waving, dyeing, or bleaching, or the form of rinse compositions to be applied before or after dyeing, bleaching, permanents, straightening, relaxing, waving or even between the two stages of a permanent or straightening process.

Non-limiting sun care product forms include: solutions, liquids, creams, powders, lotions, gels, pastes, waxes, aerosols, sprays, mists, roll-ons, sticks, milks, emulsions, and wipes.

Non-limiting skin care product forms include: solutions, oils, lotions, creams, ointments, liquids, gels, solids, W/O emulsions, O/W emulsions, milks, suspensions, microemulsions, dispersions, microencapsulated products, sticks, balms, tonics, pastes, mists, reconstitutable products, peels, soaps, aerosols, mousses, waxes, glues, pomades, spritzes, putties, lacquers, serums, perms, powders, pencils, flakes, blush, highlighters, bronzers, concealers, and 2-way cake products.

The compositions of the invention may also take the form of skin-washing compositions, and particularly in the form of solutions or gels for the bath or shower, or of make-up removal products.

The six skin care product categories that follow next may be considered a subset of the skin and sun care products:

(1) Eye Care

Non-limiting eye care product forms include: mascaras, eye liners, eye shadows, curlers of eye lashes, eyebrow pencils, and eye pencils.

(2) Lip Care

Non-limiting lip care product forms include: lipsticks, lip balms, lip pencils, lip glosses, lip sprays, transparent lip bases, tinted lip moisturizers, and multi-functional color sticks that can also be used for cheeks and eyes.

(3) Nail Care

Non-limiting nail care product forms include: nail polishes, nail varnishes, enamels, nail varnish removers, home-manicure products such as cuticle softeners and nail strengtheners, and artificial nails.

(4) Face Care

Non-limiting face care product forms include: creams, lotions, solutions, oils, liquids, peels, scrubs, emulsions, suspensions, microemulsions, microencapsulated product, pastes, reconstitutable product, aerosols, mousses, gels, waxes, glues, pomades, spritzes, facial wet-wipes, putties, lacquers, serums, perms, powders, blush, highlighters, bronzers, masks, and concealers.

(5) Body Care

Non-limiting body care product forms include: foams, peels, masks, gels, sticks, aerosols, lotions, salts, oils, balls, liquids, powders, peels, pearls, bar soaps, liquid soaps, body washes, cleansers, scrubs, creams, flakes, other bath and shower products, shaving products, waxing products, and sanitizers.

(6) Foot Care

Non-limiting foot care product forms include: mousses, creams, lotions, powders, liquids, sprays, aerosols, gels, flakes, and scrubs.

Non-limiting oral care product forms include: toothpastes, adhesives, gums, gels, powders, creams, solutions, lotions, liquids, dispersions, suspensions, emulsions, tablets, capsules, rinses, flosses, aerosols, strips, films, pads, bandages, microencapsulated products, syrups, and lozenges.

Also contemplated are personal care compositions comprising polymer(s) described herein complexed with iodine. These compositions may be used in treating skin conditions, non-limiting examples of which include dermatitis, wounds, bacterial infections, burns, rashes, and herpes. These complexed compositions may be staining, substantially non-staining, or essentially non-staining.

Examples of related personal care compositions are disclosed in U.S. Pat. Nos. 5,599,800; 5,650,166; 5,916,549; and 6,812,192; U.S. patent application 2009/0317432; EP 556,660; 661,037; 661,038; 662,315; 676,194; 796,077; 970,682; 976383; 1,415,654; and 2,067,467; and WO 2005/032506; each of which is hereby incorporated in its entirety by reference.

It is also contemplated that the personal care compositions may be used in products for male and/or female personal grooming and/or toiletry such as: sanitary napkins, baby diapers, adult diapers, feminine products, products for incontinence, and other related products.

An array of additional personal care compositions, methods, and uses are contemplated. Disclosure of these compositions may be found in the following brochures by Ashland Specialty Ingredients, each of which is hereby incorporated in its entirety by reference: *Plasdone™ K-29/32, Advanced non-oxidative, non-abrasive teeth whitening in toothpastes, mouthwashes, and oral rinses* (2010), *Polymers for oral care, product and applications guide* (2002), *A formulation guide for excellent hair styling gels and lotions* (April 2003), *PVP (polyvinylpyrrolidone)* (no date provided), and *Textile chemicals, solutions for the most challenging product environment* (no date provided).

Also contemplated are additional personal care compositions that may comprise the polymers described herein. Disclosures on such compositions may be found in the publications listed below, each of which is hereby incorporated in its entirety by reference: (1) Prototype Formulations—Personal Care Products (2009) from Xiameter, Dow Corning. (2) Sun care formulations under the category "Refreshing Sun", "Younger Sun", "Sun for Men", and "Sunny Glow" from Dow Corning. (3) Cosmetic Nanotechnology, Polymers and Colloids in Cosmetics, 2007, ACS Symposium Series. (4) Review Paper: Lipid nanoparticles (SLN, NLC) in cosmetic and pharmaceutical dermal products, International Journal of Pharmaceutics, Volume 366, 2009.

Optional: Additional Composition Ingredients

It is also contemplated that the personal care compositions optionally may contain one or more additional ingredients.

Further, it is contemplated that the composition ingredients may be formulated in a single container, or the ingredients may be formulated in-part in two or more distinct containers of the same or different type, the contents of which may require mixing prior to use.

Furthermore, it also is contemplated that the compositions may be prepared in the form of concentrates that may be diluted by a suitable substance(s) prior to use. The concentrate may, in turn, be present in any of the forms as described under 'Product Forms' for the personal care compositions of the invention.

A non-limiting list of classes of additional ingredients that may optionally be present in different types of personal care compositions is provided below: conditioning agents, antimicrobials, protectives (for example, antiradical agents), abrasives, UV absorbers, emulsifiers (including, but not limited to ethoxylated fatty acids, ethoxylated glyceryl esters, ethoxylated oils, ethoxylated sorbitan esters, fatty esters, PEG esters, polyglycerol esters), antiperspirants (including, but not limited to aluminium chlorohydrates, aluminium zirconium chlorhydrates), antioxidants, vitamins and/or provitamins, botanicals, fixatives, oxidizing agents, reducing agents, dyes, cleansing agents, anionic, cationic, nonionic, and/or amphoteric surfactants, thickeners and/or gelling agents, perfumes, flavors, and/or fragrances, pearlizing agents, stabilizers, pH adjusters, filters, antimicrobial agents, preservatives and/or disinfectants, associative polymers, oils of vegetable, mineral, and/or synthetic origin, polyols, silicones, colorants, bleaching agents, highlighting agents, propellants (including, but not limited to hydrocarbons, dimethyl ether, fluorocarbons), styling polymers, benefit agents, skin tighteners (including, but not limited to arbutin and kojic acids), tanning agents (including, but not limited to dihydroxyacetone), solvents and/or cosolvents, diluents, essential oils, sequestrants and/or chelators, carriers, and natural extracts and/or natural products.

The amount of each ingredient in the composition varies depending on the type of composition, the function and/or physicochemical property of the ingredient, and the amount of other co-ingredients. The precise amount of each ingredient may be easily determined by any person skilled in the related arts.

It may be desirable to include one or more ingredients described in the prior art disclosures IPCOM000186541D, IPCOM000128968D, and IPCOM000109682D on www.ip.com, the contents of each of these disclosures are hereby incorporated in their entirety by reference.

Further reference to formulary co-ingredients and product forms include the disclosures in US 2010/0183532, paragraphs [0096]-[162], and WO 2010/105050, paragraphs [0053]-[0069], the contents of which are hereby incorporated in their entirety by reference.

Non-limiting examples of structurants that may be used in the hair care compositions according to the invention include dextrin palmitate, trihydroxystearin, hydroxy stearic acid, hydrophilic or hydrophobic silica, hydrophobically modified clay selected from the group consisting of stearalkonium hectorite, quaternium-18 bentonite, quaternium-18 hectorite, disteardimonium hectorite, derivatives thereof, and mixtures thereof.

The hair care compositions of the invention may additionally comprise one or more hair styling agents, hair fixative agents, and/or film formers.

Particularly useful as styling agents are hair styling polymers. The hair styling polymers may be cationic, anionic, amphoteric or nonionic in nature. The polymers may be synthetic or naturally derived. Non-limiting examples of hair styling polymers include the following polymer products available for sale from Ashland Specialty Ingredients: (1) Cationic styling polymers with hair conditioning benefits—Styleze™ W Polymer, Styleze™ CC-10 (pseudo cationic), Gafquat™ 755 NP, and Gafquat™ 440; (2) Styling polymers with excellent high humidity curl retention—Styleze™ 2000, Allianz™ LT 120, Styleze™ W Polymer, and Advantage™ LCA; (3) Non-ionic styling polymers with broad ingredient compatibility—Polyvinylpyrrolidones such as PVP K-30, PVP K-60 and PVP K-90, Vinylpyrrolidone/vinyl acetate copolymers such as PVP/VA (E, I or W) 735, PVP/VA (E or W) 635, PVP/VA (E or I) 535, PVP/VA (E or I) 335 and PVP/VA S-630, and poly(vinylpyrrolidone/dimethylaminoethylmethacrylate) polymers such as Copolymer 845/937. Additional details on the aforementioned polymers and methods of use, or formulations thereof, may be found in a publication from Ashland Specialty Ingredients titled "*A Formulation Guide for Excellent Hair Styling Gels and Lotions*" (2002) that is hereby incorporated in its entirety by reference.

A non-limiting example of hair fixative agent that may be used in hair care compositions according to the invention includes a hair fixative polymer available for sale from Ashland Specialty Ingredients, AquaStyle™ 300 (INCI name Polyquaternium-69). A related publication from Ashland Specialty Ingredients titled "*Aquastyle™ 300, A Fixative Polymer with Enhanced Styling Benefits*" (2007) is hereby incorporated in its entirety by reference.

Non-limiting examples of film formers that may be used in hair care compositions according to the invention include film forming polymers available for sale from Ashland Specialty Ingredients such as (1) Aquaflex™ FX 64, (2) AquaCat™ clear cationic solution, (3) Aqualon™ carboxymethylcellulose, (4) Klucel™ hydroxypropylcellulose, and (5) Primaflo™ HP22 polymer solution.

Further details on hair styling agents, hair fixative agents, and/or film formers may be found in U.S. Pat. Nos. 7,871,600, 7,205,271, 7,122,175, 7,041,281, 6,998,114, 6,749,836, 6,689,346, 6,599,999, 6,562,325, 6,413,505, 6,387,351, 6,228,352, 5,643,581, 5,922,312, 5,897,870, 5,879,669, 5,709,850, 5,753,216 and 5,632,977 each of which is hereby incorporated in its entirety by reference.

Non-limiting examples of anti-frizz agents that may be used in hair care compositions according to the invention include anti-frizz polymers available for sale from Ashland Specialty Ingredients such as AquaStyle™ 300 and Styleze™ XT3. Information on related anti-frizz agents may be found in U.S. Pat. Nos. 7,914,773, 7,785,575, and U.S. published application 2010/00093584, the disclosures of each of which is hereby incorporated in its entirety by reference.

One or more plasticizers or coalescing agents may be added to modify the film forming characteristics of hair care compositions according to the invention. Non-limiting examples of plasticizers include glycols, adipic esters, phthalate esters, isobutyrate esters, terephthalate esters, epoxidized butyl esters or fatty acids, epoxidized vegetable oils, glycerine, di-2-ethylhexyladipate or dioctyladipate (DOA), di-2-ethylhexyl phthalate or dioctyl phthalate (DOP), di-2-ethylhexyl terephthalate (DOTP), dicyclohexyl phthalate, diisononyl adipate, diisononylphthalate, n-butyl benzyl phthalate, 1,3-butylene glycol/adipic acid polyester, dialkyl adipate, dialkyl phthalate derivatives where the alkyl group is a $C_1$-$C_{12}$ alkyl group, di-n-hexylazelate, diphenylphthalate, tricresol phosphate, benzyl benzoate, dibutyl phosphate, tributyl phosphate, tributoxyethyl phosphate, triphenyl phosphate, butyl acetyl ricinoleate, glycerol acetyl ricinoleate, dibutyl phthalate, diethyl phthalate, dioctyl phthalate, dimethoxyethyl phthalate, diisobutyl phthalate, diamyl phthalate, dibutyl glycolate, butyl stearate, triethyl citrate, tributyl citrate, tributyl acetyl citrate, 2-hexyltriethylacetyl citrate, dibutyl tartarate, camphor, epoxidized butyl esters of linseed oil fatty acids, epoxidized linseed oil, epoxidized soya oil, propylene glycol adipate, 2,2,4-trimethyl-1,3-pentanediol diisobutyrate (TXIB), methyl abietate, cumyl acetate, dibutoxyethyl adipate, di-n-hexylazelate, glyceryl-tri-benzerate, tri-n-butylcitrate, dioctyl fumarate, triisonyl trimellitate, dioctyl isophthalate, butyl oleate, chlorinated paraffin, tricresolphosphate, dibutyl sebacate, dimethicone copolyol (Dow Corning 190), PEG-6 capric/caprylic glyceride (SOFTIGEN 767), DIACETIN, LAURAMIDE DEA (MONAMID 716), phenyl trimethicone (ABIL AV 20-1000), propylene glycol, dipropylene glycol, as well as polymeric plasticizers, and mixtures thereof. Non-limiting examples of coalescing solvents include acetone, methyl acetate, and di- or tri-propylene glycol methyl ethers, and mixtures thereof. Further examples of plasticizers may be found in U.S. Pat. Nos. 5,753,216 and 5,676,935, the disclosures of each of which are hereby incorporated in its entirety by reference.

Non-limiting examples of propellants that may be used in hair care compositions of the invention include trichlorofluoromethane, chlorodifluoromethane, 1,1-difluoroethane, dichlorotetrafluoroethane, monochlorodifluoromethane, trichlorotrifluoroethane, dimethyl ether, $C_1$-$C_4$ hydrocarbons such as methane, ethane, propane, n-butane, and isobutane, water-soluble gases such as, dimethyl ether, carbon dioxide, and/or nitrous oxide, and insoluble, compressed gases such as nitrogen, helium, and fully-fluorinated oxetanes and oxepanes, and mixtures thereof.

Non-limiting examples of penetrants that may be used in hair care compositions of the invention include lanolin compounds, protein hydrolysates, protein derivatives, and mixtures thereof.

Non-limiting examples of anti-foaming agents that may be used in hair care compositions of the invention include carrier oils, silicone oils, silicone foam inhibitors, hydrophobic silica, hydrophobic fat derivatives, waxes, water-insoluble polymers, amphiphilic components, emulsifiers, coupling agents, and mixtures thereof.

Any known conditioning agent may be used in the personal care compositions of the invention. An extensive discussion on conditioning agents may be found in the book *Conditioning Agents for Skin and Hair, Cosmetic Science and Technology Series*, Volume 21, 1999, Marcel Dekker Publishers. The contents of the book are hereby incorporated in its entirety by reference.

Conditioning agents may be chosen from synthetic oils, mineral oils, vegetable oils, fluorinated or perfluorinated oils, natural or synthetic waxes, silicones, cationic polymers, proteins and hydrolyzed proteins, cationic surfactants, ceramide type compounds, fatty amines, fatty acids and their derivatives, as well as mixtures of these different types of compounds.

Non-limiting examples of suitable synthetic oils include: polyolefins, e.g., poly-α-olefins, such as polybutenes, polyisobutenes, polydecenes, and blends thereof. The polyolefins may be hydrogenated.

Non-limiting examples of suitable mineral oils include hexadecane and oil of paraffin.

Non-limiting examples of suitable animal and vegetable oils include: sunflower oil, corn oil, soy oil, avocado oil, jojoba oil, squash oil, raisin seed oil, sesame seed oil, walnut oil, fish oil, glycerol tricaprocaprylate, purcellin oil, liquid jojoba, and blends thereof. Also suitable are natural oils such as oils of eucalyptus, lavender, vetiver, litsea cubeba, lemon, sandalwood, rosemary, chamomile, savory, nutmeg, cinnamon, hyssop, caraway, orange, geranium, cade, bergamot, and blends thereof.

The conditioning agent may be a fluorinated or a perfluorinated oil. The fluoridated oils may also be fluorocarbons such as fluoramines, e.g., perfluorotributylamine, fluoridated hydrocarbons such as perfluorodecahydronaphthalene, fluoroesters, fluoroethers, and blends thereof.

Non-limiting examples of suitable natural and synthetic waxes include: carnauba wax, candelila wax, alfa wax, paraffin wax, ozokerite wax, vegetable waxes such as olive wax, rice wax, hydrogenated jojoba wax, absolute flower waxes such as black currant flower wax, animal waxes such as bees wax, modified bees wax (cerabellina), marine waxes and polyolefin waxes such as polyethylene wax, and blends thereof.

The conditioning agent may be any silicone known by those skilled in the art. Silicones include polyorganosiloxanes that are insoluble in the composition. The silicones may be present in the form of oils, waxes, resins, or gums. They may be volatile or non-volatile.

Non-limiting examples of suitable silicones include: polyalkyl siloxanes, polyaryl siloxanes, polyalkyl aryl siloxanes, silicone gums and resins, polyorgano siloxanes modified by organofunctional groups, and blends thereof.

Suitable polyalkyl siloxanes include polydimethyl siloxanes with terminal trimethyl silyl groups or terminal dimethyl silanol groups (dimethiconol) and polyalkyl (C1-C20) siloxanes. Suitable polyalkyl aryl siloxanes include polydimethyl methyl phenyl siloxanes and polydimethyl diphenyl siloxanes. The siloxanes can have a linear or branched structure.

Suitable silicone gums include polydiorganosiloxanes, such as those having a number-average molecular weight between 200,000 Da and 1,000,000 Da used alone or mixed with a solvent.

Non-limiting examples of suitable silicone gums include: polymethyl siloxane, polydimethyl siloxane/methyl vinyl siloxane gums, polydimethyl siloxane/diphenyl siloxane, polydimethyl siloxane/phenyl methyl siloxane, polydimethyl siloxane/diphenyl siloxane/methyl vinyl siloxane, and blends thereof.

Non-limiting examples of suitable silicone resins include silicones with a dimethyl/trimethyl siloxane structure and resins of the trimethyl siloxysilicate type.

The organo-modified silicones suitable for use in the invention include silicones such as those previously defined and containing one or more organofunctional groups attached by means of a hydrocarbon radical, and grafted silicone polymers. The organo-modified silicones may be one from the amino functional silicone family.

The silicones may be used in the form of emulsions, nano-emulsions, or microemulsions.

The cationic polymers that may be used as conditioning agents according to the invention generally have a molecular weight (average number) from about 500 Da to about 5,000,000 Da, and particularly from about 1,000 Da to about 3,000,000 Da. The expression "cationic polymer" as used herein indicates any polymer having at least one cationic group.

The cationic polymers may be chosen from among polymers containing primary, secondary, tertiary amine, and/or quaternary ammonium groups that may form part of the main polymer backbone and/or side chain(s).

Non-limiting examples of suitable cationic polymers include polyamines, polyaminoamides, and quaternary polyammonium classes of polymers, such as:

(1) homopolymers and copolymers derived from acrylic or methacrylic esters or amides. The copolymers may contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaffix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, N.J.).

(2) derivatives of cellulose ethers containing quaternary ammonium groups, such as hydroxy ethyl cellulose quaternary ammonium that has reacted with an epoxide substituted by a trimethyl ammonium group.

(3) derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.

(4) cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.

(5) polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.

(6) water-soluble polyamino amides prepared by polycondensation of an acid compound with a polyamine. These polyamino amides may be reticulated.

(7) derivatives of polyamino amides resulting from the condensation of polyalkylene polyamines with polycarboxylic acids followed by alkylation by bi-functional agents.

(8) polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.

(9) cyclopolymers of alkyl diallyl amine or dialkyl diallyl ammonium such as the homopolymer of dimethyl diallyl ammonium chloride and copolymers of diallyl dimethyl ammonium chloride and acrylamide.

(10) quaternary diammonium polymers such as hexadimethrine chloride.

(11) quaternary polyammonium polymers, including, for example, Mirapol® A 15, Mirapol® AD1, Mirapol® AZ1, and Mirapol® 175 products sold by Miranol.

(12) quaternary polymers of vinyl pyrrolidone and vinyl imidazole such as the products sold under the names Luviquat® FC 905, FC 550, and FC 370 by BASF Corporation.

(13) quaternary polyamines.

(14) reticulated polymers known in the art.

Other cationic polymers that may be used include cationic proteins or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin.

The conditioning agent may comprise a protein or hydrolyzed cationic or non-cationic protein. Non-limiting examples of suitable compounds include: hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having groups of quaternary ammonium on the polypeptide chain, including at least one C1-C18 alkyl, and blends thereof.

Non-limiting examples of suitable hydrolyzed cationic proteins include: Croquat® L, in which the quaternary ammonium groups include a C12 alkyl group, Croquat® M, in which the quaternary ammonium groups include C10-C18 alkyl groups, Croquat® S in which the quaternary ammonium groups include a C18 alkyl group, Crotein® Q in which the quaternary ammonium groups include at least one C1-C18 alkyl group, and blends thereof. These products are sold by Croda.

The conditioning agent may also comprise quaternized vegetable protein(s) such as wheat, corn, or soy proteins, non-limiting examples of which include: cocodimonium hydrolyzed wheat protein, laurdimonium hydrolyzed wheat protein, steardimonium hydrolyzed wheat protein, 2-N-stearoyl amino-octadecane-1,3-diol, 2-N-behenoyl amino-octadecane-1,3-diol, 2-N-[2-hydroxy-palmitoyl]-amino-octadecane-1,3-diol, 2-N-stearoyl amino-octadecane-1,3,4-triol, N-stearoyl phytosphingosine, 2-N-palmitoyl amino-hexadecane-1,3-diol, bis-(N-hydroxy ethyl N-cetyl) malonamide, N-(2-hydroxy ethyl)-N-(3-cetoxyl-2-hydroxy propyl) amide of cetylic acid, N-docosanoyl N-methyl-D-glucamine, and blends thereof.

The conditioning agent may also comprise a cationic surfactant such as a salt of a primary, secondary, or tertiary fatty amine, optionally polyoxyalkylenated, a quaternary ammonium salt, a derivative of imadazoline, or an amine oxide. Conditioning agents may also be selected from the group consisting of: mono-, di-, and tri-alkyl amines, and quaternary ammonium compounds with a counterion such as a chloride, a methosulfate, a tosylate, etc. Non-limiting examples of suitable amines include: cetrimonium chloride, dicetyldimonium chloride, behentrimonium methosulfate, and blends thereof.

The conditioning agent may comprise a fatty amine. Non-limiting examples of suitable fatty amines include: dodecyl amines, cetyl amines, stearyl amines such as stearamidopropyl dimethylamine, and blends thereof.

The conditioning agent may comprise a fatty acid or derivative(s) thereof. Non-limiting examples of suitable fatty acids include: myristic acid, palmitic acid, stearic acid, behenic acid, oleic acid, linoleic acid, isostearic acid, and blends thereof. The derivatives of fatty acids include carboxylic ester acids including mono-, di-, tri- and tetra-carboxylic acids esters, amides, anhydrides, esteramides, imides, and mixtures of these functional groups.

Also suitable as conditioning agents are the following commercial products:

(1) Aquacat™ Clear Cationic Solution (INCI Name: guar hydroxypropyltrimonium Chloride), N-Hance™ SP-100 (INCI Name: acrylamidopropyl trimonium chloride/acrylamide copolymer), and N-Hance™ cationic guar (INCI Name: guar hydroxypropyltrimonium chloride) from Ashland Specialty Ingredients (2) Salcare® from BASF Corp.

(3) Softcat™ Polymers from The Dow Chemical Company.

(4) Jaguar® C500, Polycare® Boost, Mackconditioner™ Brite, and Mackine® 301 from Rhodia.

(5) Stepanquat® ML, Stepanquat® GA-90, Ninol®, and Ammonyx® from Stepan Company.

(6) Conditioneze™ 7 and Conditioneze™ NT-20 from Ashland Specialty Ingredients (Wayne, N.J.).

Of course, mixtures of two or more conditioning agents may be used.

The conditioning agent(s) may be present in an amount from about 0.001% to about 20%, particularly from about 0.01% to about 10%, and even more particularly from about 0.1% to about 3% by weight of the composition.

Personal care compositions may optionally comprise antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bisbiquanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, N-tetradecyl-4-ethyl pyridinium chloride, dodecyl dimethyl (2-phenoxyethyl)ammonium bromide, benzyl dimethylstearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In particular embodiments, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In particular embodiments, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Polysaccharides, such as gum Arabic, may be included as well.

Personal care compositions may comprise liquid or liquid-like carrier(s) that help to distribute, disperse, and/or dissolve the ingredients.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

In one of the embodiment, the compositions of the invention may be anhydrous.

Typically, sun care compositions may also comprise one or more UV actives, which include organic and inorganic materials that scatter, absorb, and/or reflect radiation having a wavelength from about 100 nm to about 400 nm.

In one particular embodiment, the sun care compositions protect against UV-A, UV-B, and/or UV-C radiation.

UV-A radiation, from about 320 nm to about 400 nm, has the longest wavelengths within the UV spectrum, and consequently is the least energetic. UV-A radiation includes UV-A1 (from about 340 nm to about 400 nm) and UV-A2 (from about 320 nm to about 340 nm). UV-B radiation has shorter wavelengths, from about 290 nm to about 320 nm UV-C radiation has the shortest wavelengths from about 200 nm to about 290 nm.

In another embodiment, the sun care compositions may not contain UV actives, and may be regarded as tanning oils or tan promoters.

Sun care compositions may be formulated, for example, for application to the lips, hair, face, cheeks, neck, area around the eyes, full hands, and body area. Self-tanning compositions, which are products that color skin without requiring full sun exposure, also fit under the sun care umbrella.

Suitable UV absorber(s) that may be included in the personal care compositions most likely will depend on local regulations. As the rules governing the names and usage levels evolve over time, it is impossible to include every UV absorber that may be used with the invention.

Non-limiting examples of suitable UV absorbers include: octyl salicylate; pentyl dimethyl PABA; octyl dimethyl PABA; benzophenone-1; benzophenone-6; 2-(2H-benzotriazole-2-yl)-4,6-di-tert-pentylphenol; ethyl-2-cyano-3,3-diphenylacrylate; homomenthyl salicylate; bis-ethylhexyloxyphenol methoxyphenyl triazine; methyl-(1,2,2,6,6-pentamethyl-4-piperidyl)-sebacate; 2-(2H-benzotriazole-2-yl)-4-methylphenol; diethylhexyl butamido triazone; amyl dimethyl PABA; 4,6-bis(octylthiomethyl)-o-cresol; CAS number 65447-77-0; red petroleum; ethylhexyl triazone; octocrylene; isoamyl-p-methoxycinnamate; drometrizole; titanium dioxide; 2,4-di-tert-butyl-6-(5-chloro-2H-benzotriazole-2-yl)-phenol; 2-hydroxy-4-octyloxybenzophenone; benzophenone-2; diisopropyl methylcinnamate; PEG-PABA; 2-(1,1-dimethylethyl)-6-[[3-(1,1-demethylethyl)-2-hydroxy-5-methylphenyl]methyl-4-methylphenyl acrylate; drometrizole trisiloxane; menthyl anthranilate; butyl methoxydibenzoylmethane; 2-ethoxyethyl p-methoxycinnamate; benzylidene camphor sulfonic acid; dimethoxyphenyl-[1-(3,4)]-4,4-dimethyl 1,3-pentanedione; zinc oxide; N,N'-hexane-1,6-diylbis[3-(3,5-di-tert-butyl-4-hydroxyphenylpropionamide)]; pentaerythritol tetrakis[3-(3,5-di-tert-butyl-4-hydroxyphenyl)propionate]; 2,6-di-tert-butyl-4-[4,6-bis(octylthio)-1,3,5-triazin-2-ylamino]phenol; 2-(2H-benzotriazole-2-yl)-4,6-bis(1-methyl-1-phenylethyl)phenol; trolamine salicylate; diethylanolamine p-methoxycinnamate; polysilicone-15; CAS number 152261-33-1; 4-methylbenzylidene camphor; bisoctrizole; N-phenyl-benzenamine; reaction products with 2,4,4-trimethylpentene; sulisobenzone; (2-ethylhexyl)-2-cyano-3,3-diphenylacrylate; digalloyl trioleate; polyacrylamido methylbenzylidene camphor; glyceryl ethylhexanoate dimethoxycinnamate; 1,3-bis-[(2'-cyano-3',3'-diphenylacryloyl)oxy]-2,2-bis-{[(2'-cyano-bis-(2,2,6,6-tetramethyl-4-piperidyl)-sebacate; benzophenone-5; 1,3,5-tris(3,5-di-tert-butyl-4-hydroxybenzyl)-1,3,5-triazine-2,4,6(1H,3H,5H)-trione; hexamethylendiamine; benzophenone-8; ethyl-4-bis(hydroxypropyl)aminobenzoate; 6-tert-butyl-2-(5-chloro-2H-benzotriazole-2-yl)-4-methylphenol; p-aminobenzoic acid; 3,3',3'',5,5',5''-hexa-tert-butyl-α-α'-α''-(mesitylene-2,4,6-triyl)tri-p-cresol; lawsone with dihydroxyacetone; benzophenone-9; benzophenone-4; ethylhexyl dimethoxy benzylidene dioxoimidazoline propionate; N,N'-bisformyl-N,N'-bis-(2,2,6,6-tetramethyl-4-piperidinyl)-; 3-benzylidene camphor; terephthalylidene dicamphor sulfonic acid; camphor benzalkonium methosulfate; bisdisulizole disodium; etocrylene; ferulic acid; 2-(2H-benzotriazole-2-yl)-4-(1,1,3,3-tetramethylbutyl)-phenol; 4,6-bis(dodecylthiomethyl)-o-cresol; β-2-glucopyranoxy propyl hydroxy benzophenone; phenylbenzimidazole sulfonic acid; benzophenone-3; diethylamine hydroxybenzoyl hexylbenzoate; 3',3'-diphenylacryloyl)oxy]methyl}-propane; ethylhexyl p-methoxycinnamate, and blends thereof.

Personal care compositions may comprise antioxidant(s) and/or antiradical protecting agent(s).

Non-limiting examples of suitable antioxidants and/or antiradical protecting agents include: BHA (tert-butyl-4-hydroxy anisole), BHT (2,6-di-tert-butyl-p-cresol), TBHQ (tert-butyl hydroquinone), polyphenols such as proanthocyanodic oligomers, flavonoids, hindered amines such as tetra amino piperidine, erythorbic acid, polyamines such as spermine, cysteine, glutathione, superoxide dismutase, lactoferrin, and blends thereof.

Personal care compositions may comprise vitamin(s), provitamin(s), and/or mineral(s).

Non-limiting examples of suitable vitamins include: ascorbic acid (vitamin C), vitamin E, vitamin E acetate, vitamin E phosphate, B vitamins such as B3 and B5, niacin, vitamin A, derivatives thereof, and blends thereof.

Non-limiting examples of suitable provitamins include: panthenol, retinol, and blends thereof.

Non-limiting examples of suitable minerals include: talc, clay, calcium carbonate, silica, kaolin, mica, and blends thereof. Further examples of minerals that may be used in the personal care compositions may be found in a brochure titled *Minerals for Personal Care* from Imerys Performance Minerals, the disclosure of which is hereby incorporated in its entirety by reference.

Personal care compositions may comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepanol® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is incorporated hereby in its entirety by reference.

Personal care compositions may be also be formulated as detergent compositions, such as shampoos, bath gels, and bubble baths. Such compositions comprise water as a liquid carrier. The surfactant or surfactants that form the washing base may be chosen alone or in blends, from known anionic, amphoteric, zwitterionic and/or non-ionic surfactants. The quantity and quality of the washing base must be sufficient to impart a satisfactory foaming and/or detergent value to the final composition. The washing base may be present in an amount from about 4% to about 50% by weight, particularly from about 6% to about 35% by weight, and more particularly from about 8% to about 25% by weight of the final composition.

Personal care compositions may comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; arachis hypogaea (peanut) flour; ascorbyl methylsilanol pectinate; astragalus gummifer gum; attapulgite; avena sativa (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; caesalpinia spinosa gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; ceratonia siliqua gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium dulcis (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked bacillus/glucose/sodium glutamate ferment; cyamopsis tetragonoloba (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; distearteth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™MG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; *sclerotium* gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate;

sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; *sterculia urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, N-Hance™ cationic guar, N-Hance™ HP Series hydroxypropyl guar, N-Hance™ SP-100 conditioning polymer, and Supercol™ guar gum from Ashland Specialty Ingredients (2) Carbopol Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients (Wayne, N.J.).

Also suitable as a thickener/rheology modifier are lightly- to moderately-crosslinked polyvinylpyrrolidones. Disclosures of these polymers are provided in the following publications, each of which is hereby incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

Personal care compositions may comprise natural extracts and/or natural products. Extensive details on natural products that can be used in personal care compositions is provided in book chapter "Chemistry of Cosmetics, Comprehensive Natural Products II" in Chemistry and Biology; volume 3, 2010.

Oral Care Composition Ingredients

Oral care compositions may optionally contain one or more additional ingredients. Non-limiting examples of suitable ingredients include: carriers, dentifrices, cleaning agents, breath freshening actives, pain relievers, anesthetics, anti-inflammatory agents, antimicrobial agents, antibacterial agents, anti-calculus agents, anti-plaque agents, gums, thickeners, gelling agents, surfactants, flavors, warming or tingling agents, tooth bleaching agents, whiteners, stain removers, stain preventers, abrasives, adhesives, colors, emollients, emulsifiers, preservatives, solvents, binders, stimulants, depressants, diet aids, smoking cessation aides, vitamins, minerals, throat-soothing agents, spices, herbs, herbal extracts, alkaloids (such as caffeine and nicotine), and humectants.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, as disclosed in e.g., U.S. Pat. No. 3,988,433. Carrier materials for biphasic dentifrice formulations are disclosed in U.S. Pat. Nos. 5,213,790; 5,145,666; 5,281,410; 4,849,213; and 4,528,180. Mouthwash, rinse or mouth spray carrier materials typically include water, flavoring and sweetening agents, etc., as disclosed in, e.g., U.S. Pat. No. 3,988,433. Lozenge carrier materials typically include a candy base; chewing gum carrier materials include a gum base, flavoring and sweetening agents, as in, e.g., U.S. Pat. No. 4,083,955. Sachet carrier materials typically include a sachet bag, flavoring and sweetening agents. For sub-gingival gels used for delivery of actives into the periodontal pockets or around the periodontal pockets, a "sub-gingival gel carrier" is chosen as disclosed in, e.g., U.S. Pat. Nos. 5,198,220 and 5,242,910. The selection of a carrier will depend on secondary considerations like taste, cost, and shelf stability, and other factors.

Oral care compositions may comprise one or more dental abrasives. Dental abrasives useful in the compositions include many different materials. The material selected must be one which is compatible within the composition of interest and does not excessively abrade dentin.

Non-limiting examples of suitable abrasives include: silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, resinous abrasive materials such as particulate condensation products of urea and formaldehyde, and blends thereof.

Another class of abrasives is the particulate thermosetting polymerized resins as described in U.S. Pat. No. 3,070,510.

Non-limiting examples of suitable resins include: melamines, phenolics, ureas, melamine-ureas, melamine-formaldehydes, urea-formaldehyde, melamine-urea-formaldehydes, cross-linked epoxides, cross-linked polyesters, and blends thereof.

Silica dental abrasives of various types may be employed because of their unique benefits of exceptional dental cleaning and polishing performance without unduly abrading tooth enamel or dentine. The silica abrasive polishing materials herein, as well as other abrasives, generally have an average particle size ranging from about 0.1 to about 30 microns, and particularly from about 5 to about 15 microns. The abrasive can be precipitated silica or silica gels such as the silica xerogels described in U.S. Pat. No. 3,538,230, and U.S. Pat. No. 3,862,307.

Non-limiting examples of suitable silica abrasives include: silica xerogels marketed under the trade name "Syloid" by the W.R. Grace & Company, Davison Chemical Division and precipitated silica materials such as those marketed by the J.M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the invention are described in more detail in U.S. Pat. Nos. 4,340,583; 5,603,920; 5,589,160; 5,658,553; 5,651,958; and 6,740,311. Each of these disclosures is hereby incorporated in its entirety by reference.

Mixtures of abrasives can be used such as mixtures of the various grades of Zeodent® silica abrasives listed above.

The total amount of abrasive(s) in the oral care compositions typically range from about 6% to about 70% by weight; toothpastes may contain from about 10% to about 50% of abrasives by weight of the composition. Dental solution, mouth spray, mouthwash and non-abrasive gel compositions typically contain little or no abrasives.

Oral care compositions may comprise polymeric mineral surface active agent(s) (PMSAs). PMSAs include any agent which will have a strong affinity for the tooth surface, deposit a polymer layer or coating on the tooth surface and produce the desired surface modification effects. The "mineral" descriptor is intended to convey that the surface activity or substantivity of the polymer is toward mineral surfaces such as calcium phosphate minerals or teeth.

Non-limiting examples of suitable PMSAs include: polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate), poly(vinyl benzyl chloride), polycarboxylates, carboxy-substituted polymers, and blends thereof. Also suitable as polymeric mineral surface active agents are the carboxy-substituted alcohol polymers described in U.S. Pat. Nos. 5,292,501; 5,213,789, 5,093,170; 5,009,882; and 4,939,284; and the diphosphonate-derivatized polymers in U.S. Pat. No. 5,011,913; the synthetic anionic polymers including polyacrylates and copolymers of maleic anhydride or acid and methyl vinyl ether (e.g., Gantrez®), as described, for example, in U.S. Pat. No. 4,627,977. Another example of a polymeric mineral surface active agent is a diphosphonate modified polyacrylic acid.

Polymers with activity must have sufficient surface binding propensity to desorb pellicle proteins and remain affixed to enamel surfaces. For tooth surfaces, polymers with end or side chain phosphate or phosphonate functions may be used, although other polymers with mineral binding activity may prove effective depending upon adsorption affinity.

PMSAs are useful in the compositions because of their stain prevention benefit. It is believed the PMSAs provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSAs on teeth can also prevent stains from accruing due to disruption of binding sites of color bodies on tooth surfaces.

The ability of PMSA to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers. The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

Oral care compositions may comprise additional anticalculus agent(s), such as a pyrophosphate salt as a source of pyrophosphate ion.

Non-limiting examples of suitable pyrophosphate salts include: dialkali metal pyrophosphate salts, tetraalkali metal pyrophosphate salts, and mixtures thereof. Particularly, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may find utility.

In compositions of the invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, particularly from about 1.5% to about 10%, and more particularly from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, particularly less than about 10% of the total pyrophosphate dissolved in the composition. Tetrasodium pyrophosphate salt may be one such pyrophosphate salt in these compositions. Tetrasodium pyrophosphate may be the anhydrous salt form or the decahydrate form, or any other species stable in solid form in the oral care compositions. The salt is in its solid particle form, which may be its crystalline and/or amorphous state, with the particle size of the salt being small enough to be aesthetically acceptable and readily soluble during use. The amount of pyrophosphate salt useful in making these compositions is any tartar control effective amount, generally from about 1.5% to about 15%, particularly from about 2% to about 10%, and more particularly from about 3% to about 8% by weight of the oral care composition.

The pyrophosphate salts are described in more detail in *Kirk-Othmer Encyclopedia of Chemical Technology*, third edition, volume 17, Wiley-Interscience Publishers (1982).

Oral care compositions may comprise peroxide compounds.

Non-limiting examples of suitable peroxide compounds include: hydrogen peroxide and organic peroxides including urea peroxide, carbamide peroxide, glyceryl peroxide, benzoyl peroxide, derivatives thereof, and blends thereof.

Typically, the peroxide compound can be employed in amounts so that at least about 1% by weight of the composition comprises peroxide. The peroxide compound may comprise from about 2% to about 30% by weight of the composition. More particularly, the peroxide comprises from about 3% to about 15% by weight of the composition. A typical peroxide concentration in the composition is generally from about 2% to about 7% by weight for home use products, and from about 15% to about 20% by weight for dental professional use.

Thickening or gelling agents used in dentifrice compositions may include nonionic polyoxyethylene polyoxypropylene block copolymers. Illustrative of polyoxyethylene polyoxypropylene block copolymers useful in the practice include block copolymers having the formula $HO(C_2H_4O)_b(C_3H_6O_6)_a(C_2H_4O)_bH$ wherein a is an integer such that the hydrophobic base represented by $(C_3H_6O_6)$ has a molecular weight of about 2,750 Da to 4000 Da, b is an integer such that the hydrophilic portion (moiety) represented by $(C_2H_4O)$ constitutes from about 70% to about 80% by weight of the copolymer. Block copolymers of this composition are available commercially under the trademark Pluronic® F type.

Pluronic® F127 has a molecular weight of 4,000 Da and contains 70% of the hydrophilic polyoxyethylene moiety.

Also suitable as a thickening agent is lightly- to moderately-crosslinked PVP, described in international application PCT/US11/30642.

The thickening agents may be present in an amount from about 15% to about 50% by weight, particularly from about 25% to about 45% by weight of the composition.

Surfactants may also be included in the oral care compositions of the invention, where they may serve in solubilizing, dispersing, emulsifying and/or reducing the surface tension of the teeth in order to increase the contact between the tooth and the peroxide. The compositions may also comprise surfactants, also commonly referred to as sudsing agents. Suitable surfactants are those which are reasonably stable and foam throughout a wide pH range. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type. Many suitable anionic surfactants are disclosed in U.S. Pat. No. 3,959,458. The compositions may comprise an anionic surfactant in an amount from about 0.025% to about 9% by weight, particularly from about 0.05% to about 5% by weight, and more particularly from about 0.1% to about 1% by weight of the composition.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate. The sarcosinate surfactant may be present in the compositions from about 0.1% to about 2.5%, particularly from about 0.5% to about 2.0% by weight of the total composition.

Non-limiting examples of suitable cationic surfactants include: derivatives of aliphatic quaternary ammonium compounds having at least one long alkyl chain containing from about 8 to about 18 carbon atoms such as lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Also suitable are the quaternary ammonium fluorides described in U.S. Pat. No. 3,535,421, where the quaternary ammonium fluorides have detergent properties. Certain cationic surfactants can also act as germicides in the compositions disclosed herein.

Nonionic surfactants that may be used in the compositions of the invention include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Oral care compositions may comprise flavor(s).

Non-limiting examples of suitable flavors include: methyl salicylate, ethyl salicylate, methyl cinnamate, ethyl cinnamate, butyl cinnamate, ethyl butyrate, ethyl acetate, methyl anthranilate, iso-amyl acetate, iso-armyl butyrate, allyl caproate, eugenol, eucalyptol, thymol, cinnamic alcohol, cinnamic aldehyde, octanol, octanal, decanol, decanal, phenylethyl alcohol, benzyl alcohol, benzaldehyde, α-terpineol, linalool, limonene, citral, vanillin, ethyl vanillin, propenyl guaethol, maltol, ethyl maltol, heliotropin, anethole, dihydroanethole, carvone, oxanone, menthone, β-damascenone, ionone, gamma decalactone, gamma nonalactone, gamma undecalactone, 4-hydroxy-2,5-dimethyl-3(2H)-furanone, and blends thereof.

Generally suitable flavoring agents are those containing structural features and functional groups that are less prone to oxidation by peroxide. These include derivatives of flavor chemicals that are saturated or contain stable aromatic rings or ester groups.

Also suitable are flavor chemicals that may undergo some oxidation or degradation without resulting in a significant change in the flavor character or profile. The flavor chemicals, including menthol, may be provided as single or purified chemicals rather than supplied in the composition by addition of natural oils or extracts such as peppermint, spearmint, or wintergreen oils as these sources may contain other components that are relatively unstable and may degrade in the presence of peroxide. Flavoring agents are generally used in the compositions at levels of from about 0.001% to about 5% by weight of the composition.

The flavor system may typically include sweetening agent(s). Sweeteners include compounds of natural and artificial origin.

Non-limiting examples of suitable water-soluble natural sweeteners include: monosaccharides, disaccharides and polysaccharides, such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and blends thereof.

Non-limiting examples of suitable water-soluble artificial sweeteners include: soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerin and L-aspartyl-L-2,5, dihydrophenyl-glycine, L-aspartyl-2,5-dihydro-L-phenylalanine, L-aspartyl-L-(1-cyclohexyen)-alanine, derivatives thereof, and blends thereof. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) may be used. The compositions may contain sweetener(s) in an amount from about 0.1% to about 10% by weight, in particular from about 0.1% to about 1% by weight of the composition.

In addition, the flavor system may include salivating agents, warming agents, and numbing agents. These agents are present in the compositions in an amount from about 0.001% to about 10% by weight, particularly from about 0.1% to about 1% by weight of the composition.

A non-limiting example of suitable salivating agent includes Jambus® manufactured by Takasago. Non-limiting examples of suitable warming agents include *capsicum* and nicotinate esters such as benzyl nicotinate. Non-limiting examples of suitable numbing agents include benzocaine, lidocaine, clove bud oil, ethanol, and blends thereof.

Oral care compositions may comprise chelating agent(s).

The chelating agents may include metal solubilizing agents and metal precipitating agents. The metal solubilizing agents include a condensed pyrophosphate compound. For purposes of this invention "condensed phosphate" relates to an inorganic phosphate composition containing two or more phosphate species in a linear or cyclic pyrophosphate form. The condensed phosphate may be sodium pyrophosphate, but may also include tripolyphosphate, hexametaphosphate, cyclic condensed phosphate or other similar phosphates well known in the field. The blend may also include an organic chelating agent. The term "organic phosphate" includes phosphonic acid, di and tri phosphonoc acid compound or its salts. An example of phosphonic acid is 1-hydroxyethylidene-1,1-diphosphonic acid that is sold under the trade name of Dequest®. The blend may also include a metal precipitating chelating agent. The term "metal precipitating chelating agent" is an agent that binds to metals and causes the metal to precipitate and includes halogens such as fluoride. The chelating agents are incorporated in the oral care compositions of the invention in an amount from about 0.1% to about 8.0% by weight, and particularly from about 0.5% to about 3.0% by weight of the composition, in a ratio of about 3:1:1 w/w organic chelating agent: condensed phosphate chelating agent: metal precipitating agent.

Another optional ingredient that may be used in oral care compositions is a humectant. For example, a humectant may be added to keep toothpaste compositions from hardening upon exposure to air, to give compositions a moist feel to the mouth, and, for particular humectants, to impart desirable sweetness of flavor to toothpaste compositions. The humectant, on a pure humectant basis, is generally present from about 0% to about 70%, particularly from about 5% to about 25% by weight of the composition.

Non-limiting examples of suitable humectants include: edible polyhydric alcohols such as glycerin, sorbitol, xylitol, butylene glycol, polyethylene glycol, propylene glycol, trimethyl glycine, and blends thereof.

The invention also contemplates oral care compositions comprising polymer(s) described herein complexed with hydrogen peroxide. A description of such complexes is present in international application WO 91/07184, the contents of which are hereby incorporated in their entirety by reference.

Also contemplated are oral care compositions such as those described in the following patents and patent applications, the contents of each are hereby incorporated in their entirety by reference: WO 2011/068514, WO 2011/053877, US 2010/0275394, US 2011/0076090, US 2008/091935, US 2008/0181716, US 2008/0014224, WO 2007/066837, US 2008/0292669, US 2007/0071696, US 2007/0154863, US 2008/0317797, US 2005/0249678, US 2007/0178055, US 2007/0189983, WO 2005/041910, U.S. Pat. No. 7,785,572, WO 1998/005749, WO 1997/022651, and U.S. Pat. No. 5,310,563.

Oral care compositions may comprise one or more denture adhesives.

Synthetic materials presently dominate the denture adhesive market. Such materials may consist of mixtures of the salts of short-acting polymers (e.g., carboxymethylcellulose or "CMC") and long-acting polymers (e.g., poly[vinyl methyl ether maleate], or "Gantrez" and its salts). Polyvinylpyrrolidone (povidone) may also be used.

Other components of denture adhesive products impart particular physical attributes to the formulations. Petrolatum, mineral oil, and polyethylene oxide may be included in creams to bind the materials and to make their placement easier. Silicon dioxide and calcium stearate may be used in powders to minimize clumping. Menthol and peppermint oils may be used for flavoring, red dye for color, and sodium borate and methyl- or poly-paraben as preservatives.

It is also contemplated that the composition ingredients may be formulated in a single container, or the ingredients may be formulated in-part in two or more distinct containers of the same or different type, the contents of which may require mixing prior to use.

The compounds, polymers, and non-homopolymers according to the invention may be prepared according to the examples set out below. The examples are presented for purposes of demonstrating, but not limiting, the preparation of the compounds, polymers, and non-homopolymers according to the invention.

EXAMPLES

The following non-limiting examples are provided to illustrate a few of the methods for preparing the N-alkenyl hemi-aminal ethers and thioethers.

Example 1: Synthesis of Hemi-Aminal Ether of N-vinyl-2-caprolactam and 2-ethyl-1-hexanol

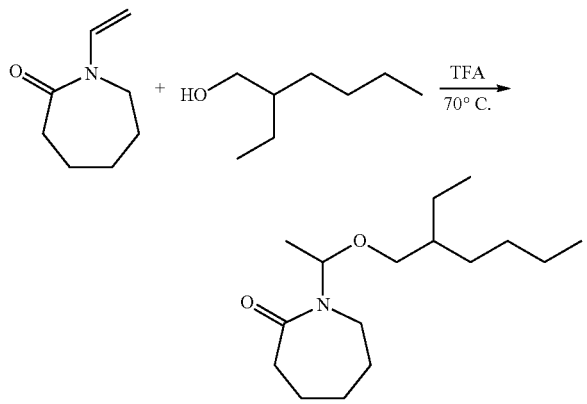

A quantity of 100.0 g of N-vinyl-2-caprolactam (0.72 mol) and 100.0 g of 2-ethyl-1-hexanol (2.17 mol) were charged into a 1-liter resin kettle, fitted with a propeller agitator, a heating mantle, a reflux condenser, and a thermocouple. The reactor was heated to 60° C. A quantity of 0.1 g of trifluoroacetic acid (TFA, 0.001 mol) was added as a Markovnikov acid catalyst into the reactor. After the initial exotherm, the reaction temperature was maintained at 70° C. for 13 hours. GC analysis was used to measure N-vinyl-2-caprolactam residual at 2 hrs, 4 hrs, 8 hrs and 13 hrs of reaction time. At 13 hrs reaction time, the reaction mixture was cooled down to room temperature and discharged. The product was purified by washing with NaHCO₃ (one extraction) and de-ionized water (three washes) to remove excess N-vinyl-2-caprolactam.

Example 2: Synthesis of Hemi-Aminal Ether of N-vinyl-2-caprolactam and 1-octanol

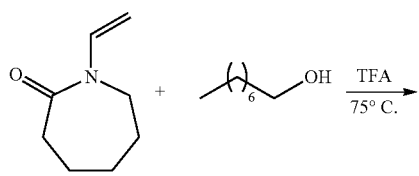

-continued

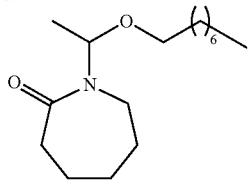

A quantity of 320.2 g of N-vinyl-2-caprolactam (2.30 mol) and 221.3 g of 1-octanol (1.70 mol) were charged into a 1-liter resin kettle, fitted with a propeller agitator, a heating mantle, a reflux condenser, and a thermocouple. The reactor was heated to 60° C. A quantity of 0.194 g of trifluoroacetic acid (TFA, 0.002 mol) was added as a Markovnikov acid catalyst into the reactor. After the initial exotherm, the reaction temperature was kept at 75° C. for 24 hours. GC analysis was used to measure 1-octanol residual at 2 hrs, 4 hrs, 8 hrs and 24 hrs. At 24 hrs reaction time, the reaction mixture was cooled down to room temperature. The product was purified by extraction with NaHCO₃ (one extraction) and de-ionized water (three extractions) to remove excess N-vinyl-2-caprolactam.

Example 3: Synthesis of Hemi-Aminal Ether of N-vinyl-2-caprolactam and 1-dodecanol

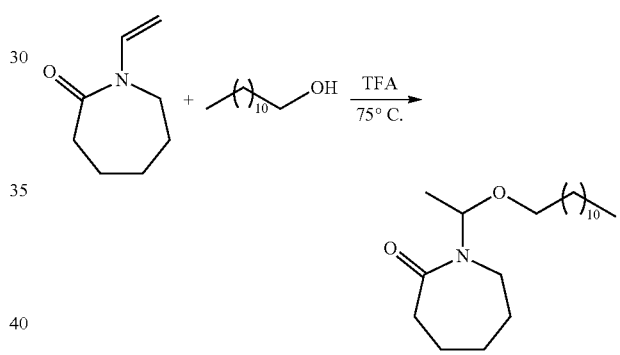

A quantity of 253.3 g of N-vinyl-2-caprolactam (1.80 mol) and 260.8 g of 1-dodecanol (1.40 mol) were charged into a 1-liter resin kettle, fitted with a propeller agitator, a heating mantle, a reflux condenser, and a thermocouple. The reactor was heated to 60° C. A quantity of 0.160 g of trifluoroacetic acid (TFA, 0.001 mol) was added as a Markovnikov acid catalyst into the reactor. After the initial exotherm, the reaction temperature was kept at 75° C. for 24 hours. GC analysis was used to measure 1-dodecanol residual at 2 hrs, 4 hrs, 8 hrs and 24 hrs. At 24 hrs reaction time, the reaction mixture was cooled down to room temperature. The product was purified by extraction with NaHCO₃ (one extraction) and de-ionized water (three extractions) to remove excess N-vinyl-2-caprolactam.

Example 4: Synthesis of Hemi-Aminal Ether of N-vinyl-2-pyrrolidone and 1-octanol

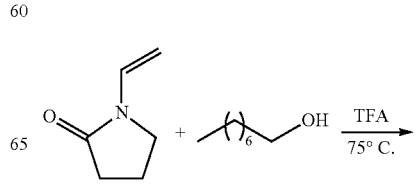

-continued

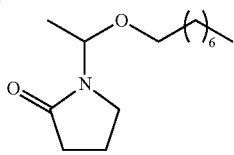

A quantity of 288.9 g of N-vinyl-2-pyrrolidone (2.60 mol) and 260.4 g of 1-octanol (2.00 mol) were charged into a 1-liter resin kettle, fitted with a propeller agitator, a heating mantle, a reflux condenser, and a thermocouple. The reactor was heated to 60° C. Then, 0.228 g of trifluoroacetic acid (TFA, 0.002 mol) was added as a Markovnikov acid catalyst into the reactor. After the initial exotherm, the reaction temperature was kept at 75° C. for 24 hours. GC analysis was used to measure 1-octanol residual at 2 hrs, 4 hrs, 8 hrs and 24 hrs. At 24 hrs reaction time, the reaction mixture was cooled down to room temperature. The product was purified by extraction with NaHCO$_3$ (one extraction) and de-ionized water (three extractions) to remove excess N-vinyl-2-pyrrolidone.

Example 5: Synthesis of Hemi-Aminal Ether of N-vinyl-2-pyrrolidone and 1-dodecanol

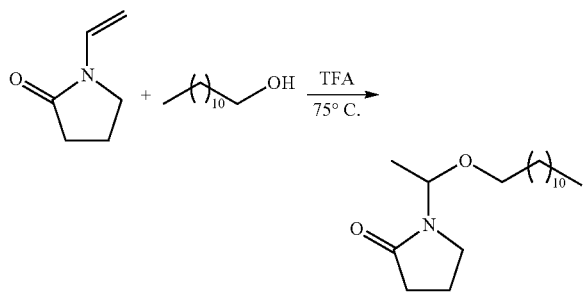

A quantity of 231.1 g of N-vinyl-2-pyrrolidone (2.10 mol) and 298.1 g of 1-dodecanol (1.60 mol) were charged into a 1-liter resin kettle, fitted with a propeller agitator, a heating mantle, a reflux condenser, and a thermocouple. The reactor was heated to 60° C. A quantity of 0.183 g of trifluoroacetic acid (TFA, 0.002 mol) was added as a Markovnikov acid catalyst into the reactor. After the initial exotherm, the reaction temperature was kept at 75° C. for 24 hours. GC analysis was used to measure 1-dodecanol residual at 2 hrs, 4 hrs, 8 hrs and 24 hrs. At 24 hrs reaction time, the reaction mixture was cooled down to room temperature. The product was purified by extraction with NaHCO$_3$ (one extraction) and de-ionized water (three extractions) to remove excess N-vinyl-2-pyrrolidone.

Example 6: Synthesis of Hemi-Aminal Ether of N-vinyl-2-caprolactam and 2-butyl-2-ethyl-1,3-propanediol

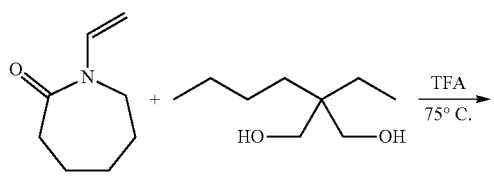

-continued

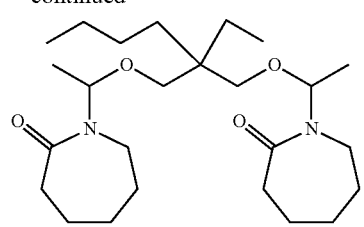

A quantity of 139.2 g of N-vinyl-2-caprolactam (1.00 mol) and 88.2 g of 2-butyl-2-ethyl-1,3-propanediol (0.55 mol) were charged into a 1-liter resin kettle, fitted with a propeller agitator, a heating mantle, a reflux condenser, and a thermocouple. The reactor was heated to 60° C. A quantity of 0.114 g of trifluoroacetic acid (TFA, 0.001 mol) was added as a Markovnikov acid catalyst into the reactor. After the initial exotherm, the reaction temperature was kept at 75° C. for 24 hours. GC analysis was used to measure N-vinyl-2-caprolactam residual at 2 hrs, 4 hrs, 8 hrs and 24 hrs. At 24 hrs reaction time, the reaction mixture was cooled down to room temperature.

Example 7: Synthesis of Hemi-Aminal Ether of N-vinyl-2-caprolactam and 1,1,1-tris(hydroxymethyl)ethane

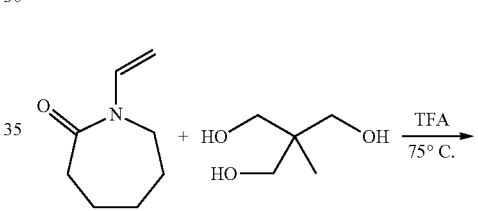

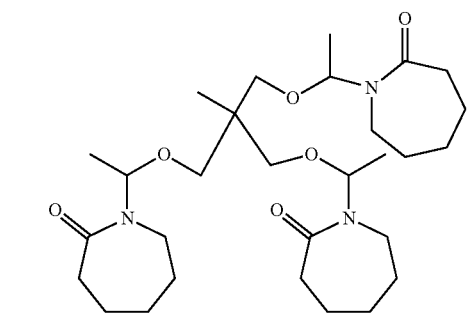

A quantity of 139.2 g of N-vinyl-2-caprolactam (1.00 mol) and 44.1 g of 1,1,1-tris(hydroxymethyl)ethane (0.37 mol) were charged into a 1-liter resin kettle, fitted with a propeller agitator, a heating mantle, a reflux condenser, and a thermocouple. The reactor was heated to 60° C. A quantity of 0.114 g of trifluoroacetic acid (TFA, 0.001 mol) was added as a Markovnikov acid catalyst into the reactor. After the initial exotherm, the reaction temperature was kept at 75° C. for 24 hours. GC analysis was used to measure N-vinyl-2-caprolactam residual at 2 hrs, 4 hrs, 8 hrs and 24 hrs. At 24 hrs reaction time, the reaction mixture was cooled down to room temperature.

Example 8: Synthesis of Hemi-Aminal Ether of N-vinyl-2-pyrrolidone and 2-butyl-2-ethyl-1,3-propanediol

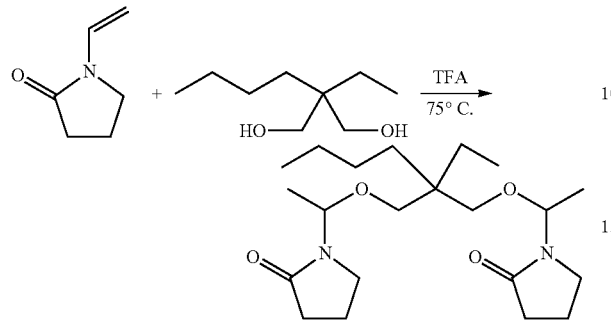

A quantity of 111.1 g of N-vinyl-2-pyrrolidone (1.00 mol) and 88.2 g of 2-butyl-2-ethyl-1,3-propanediol (0.55 mol) were charged into a 1-liter resin kettle, fitted with a propeller agitator, a heating mantle, a reflux condenser, and a thermocouple. The reactor was heated to 60° C. A quantity of 0.114 g of trifluoroacetic acid (TFA, 0.001 mol) was added as a Markovnikov acid catalyst into the reactor. After the initial exotherm, the reaction temperature was kept at 75° C. for 24 hours. GC analysis was used to measure N-vinyl-2-pyrrolidone residual at 2 hrs, 4 hrs, 8 hrs and 24 hrs. At 24 hrs reaction time, the reaction mixture was cooled down to room temperature.

Example 9: Synthesis of Hemi-Aminal Ether of N-vinyl-2-pyrrolidone and 1,1,1-tris(hydroxymethyl)ethane

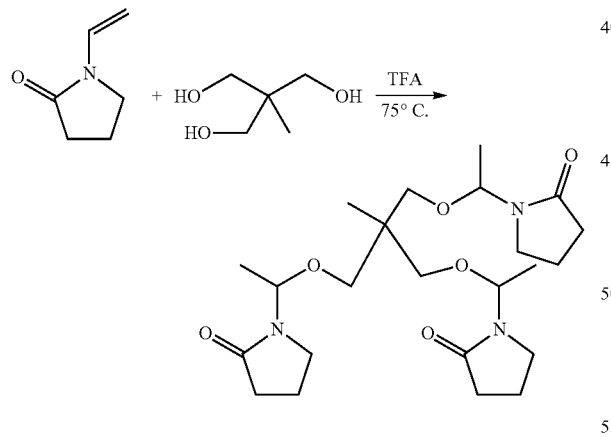

A quantity of 111.1 g of N-vinyl-2-pyrrolidone (1.00 mol) and 44.1 g of 1,1,1-tris(hydroxymethyl)ethane (0.37 mol) were charged into a 1-liter resin kettle, fitted with a propeller agitator, a heating mantle, a reflux condenser, and a thermocouple. The reactor was heated to 60° C. A quantity of 0.114 g of trifluoroacetic acid (TFA, 0.001 mol) was added as a Markovnikov acid catalyst into the reactor. After the initial exotherm, the reaction temperature was kept at 75° C. for 24 hours. GC analysis was used to measure N-vinyl-2-pyrrolidone residual at 2 hrs, 4 hrs, 8 hrs and 24 hrs. At 24 hrs reaction time, the reaction mixture was cooled down to room temperature.

Example 10: Synthesis of Hemi-Aminal Ether of N-vinyl-2-caprolactam and 2-hydroxyethyl methacrylate (HEMA)

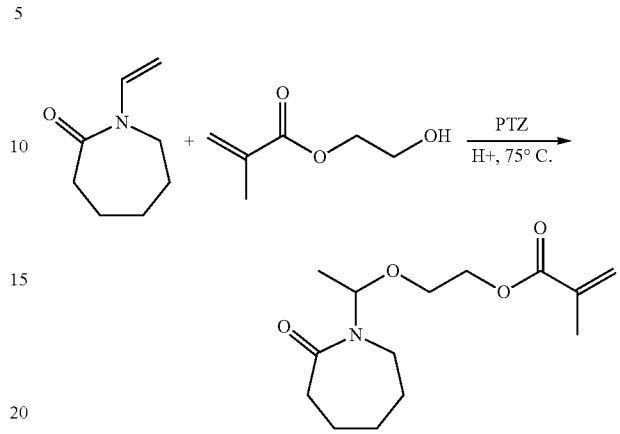

A quantity of 217.2 g of N-vinyl-2-caprolactam (1.56 mol), 169.5 g of 2-hydroxyethyl methacrylate (HEMA, 1.30 mol), 0.193 g 4-methoxyphenol (500 ppm), and 0.193 g phenothiazine (PTZ, 500 ppm) were charged into a 1-liter resin kettle, fitted with a propeller agitator, a heating mantle, a reflux condenser, and a thermocouple. The reactor was heated to 40° C. A quantity of 0.148 g of trifluoroacetic acid (TFA, 0.0013 mol) was added as a Markovnikov acid catalyst into the reactor. After the initial exotherm, the reaction temperature was kept at 75° C. for 20 hours. GC analysis was used to measure HEMA residual at 2 hrs, 4 hrs, 8 hrs and 20 hrs. At 20 hrs reaction time, the reaction mixture was cooled down to room temperature. The product was purified by extraction with $NaHCO_3$ (one extraction) and de-ionized water (three extractions) to remove excess N-vinyl-2-caprolactam.

Example 11: Synthesis of Hemi-Aminal Ether of N-vinyl-2-pyrrolidone and HEMA

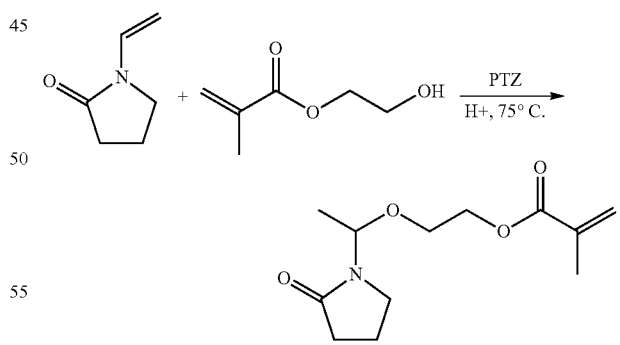

A quantity of 133.3 g of N-vinyl-2-pyrrolidone (1.20 mol), 130.4 g of HEMA (1.00 mol), 0.132 g 4-methoxyphenol (500 ppm), and 0.132 g phenothiazine (PTZ, 500 ppm) were charged into a 1-liter resin kettle, fitted with a propeller agitator, a heating mantle, a reflux condenser, and a thermocouple. The reactor was heated to 40° C. A quantity of 0.114 g of trifluoroacetic acid (TFA, 0.001 mol) was added as a Markovnikov acid catalyst into the reactor. After the initial exotherm, the reaction temperature was kept at 75° C.

for 20 hours. GC analysis was used to measure HEMA residual at 2 hrs, 4 hrs, 8 hrs and 20 hrs. At 20 hrs reaction time, the reaction mixture was cooled down to room temperature. The product was purified by extraction with NaHCO$_3$ (one extraction) and de-ionized water (three extractions) to remove excess N-vinyl-2-pyrrolidone.

Examples 12-23: Syntheses of Polymerizable N-Alkenyl Hemi-Aminal Ethers

For each of Examples 12-23, Example 11 is substantially repeated, substituting other N-alkenyl amides (first reactant) for N-vinyl-2-pyrrolidone and substituting other polymerizable compounds having at least one hydroxyl group (second reactant) for HEMA. Table 1 shows the structures of the first reactant, the second reactant and the corresponding aminal or hemi-aminal ether reaction product for each of the Examples 12-23.

One or more of the hydroxyl moiety may be replaced with a thiol moiety to yield the corresponding thioether polymerizable product.

TABLE 1

Structures of reactants and product for each of Examples 12-23

| Example | First Reactant | Second Reactant | Reaction Product |
|---|---|---|---|
| 12 | | | |
| 13 | | | |
| 14 | | | |
| 15 | | | |
| 16 | | | |
| 17 | | | |

TABLE 1-continued

Structures of reactants and product for each of Examples 12-23

| Example | First Reactant | Second Reactant | Reaction Product |
|---------|----------------|-----------------|------------------|
| 18 | N-vinyl pyrrolidone | glycerol methacrylate | adduct |
| 19 | N-vinyl caprolactam | 3-hydroxypropyl methacrylate | adduct |
| 20 | N-vinyl caprolactam | 4-hydroxybutyl methacrylate | adduct |
| 21 | 1-vinyl-2-imidazolidinone | 3-hydroxypropyl methacrylate | adduct |
| 22 | 1,3-divinyl-2-imidazolidinone | 3-hydroxypropyl methacrylate | bis-adduct |
| 23 | 4-vinyl-3-morpholinone | 3-hydroxypropyl methacrylate | adduct |
| 24 | N-vinyl pyrrolidone | N-(2-hydroxyethyl)maleimide | adduct |

TABLE 1-continued

Structures of reactants and product for each of Examples 12-23

| Example | First Reactant | Second Reactant | Reaction Product |
|---|---|---|---|
| 25 | | | |
| 26 | | | |
| 27 | | | |
| 28 | | | |
| 29 | | | |

Example 30: Synthesis of Hemi-Aminal Ether of N-vinyl-2-caprolactam and BIO-SOFT® N23-3 Alcohol Ethoxylate

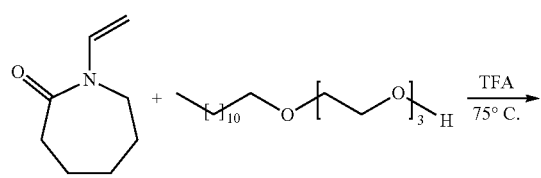

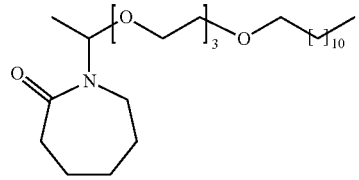

A quantity of 55.7 g of N-vinyl-2-caprolactam (0.40 mol) and 167.4 g of C12-13 Alcohol Ethoxylate (BIO-SOFT® N23-3, Stepan) (0.52 mol) were charged into a 1-liter resin kettle, fitted with a propeller agitator, a heating mantle, a reflux condenser, and a thermocouple. The reactor was heated to 65° C. Three portions of trifluoroacetic acid (TFA), each of 0.228 g (0.002 mol) were added at half hour reaction intervals. After the initial exotherm, the reaction temperature was kept at 75° C. for 24 hours. GC analysis was used to measure BIO-SOFT® N23-3 residual at 2 hrs, 4 hrs, 6 hrs, 18 hrs and 24 hrs. At 24 hrs reaction time, the reaction mixture was cooled down to room temperature.

Example 31: Synthesis of Hemi-Aminal Ether of N-vinyl-2-caprolactam BIO-SOFT® N1-3 Alcohol Ethoxylate

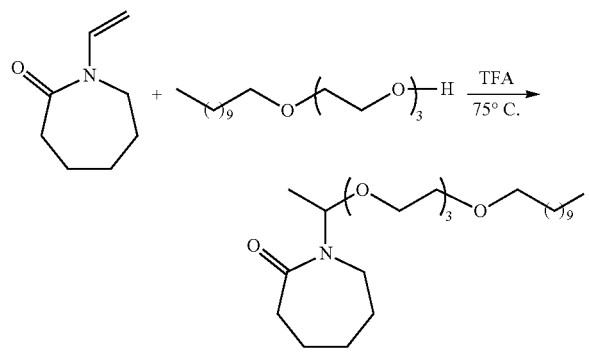

A quantity of 59.9 g of N-vinyl-2-caprolactam (0.43 mol) and 213.5 g C11 Alcohol Ethoxylate (BIO-SOFT® N1-3, Stepan) (0.70 mol) were charged into a 1-liter resin kettle, fitted with a propeller agitator, a heating mantle, a reflux condenser, and a thermocouple. The reactor was heated to 65° C. Three portions of trifluoroacetic acid (TFA), each of 0.376 g (0.0033 mol) were added at half hour reaction intervals. After the initial exotherm, the reaction temperature was kept at 75° C. for 24 hours. GC analysis was used to measure BIO-SOFT® N1-3 residual at 2 hrs, 4 hrs, 6 hrs, 18 hrs and 24 hrs. At 24 hrs reaction time, the reaction mixture was cooled down to room temperature. The product was purified by extraction with NaHCO₃ (one extraction) and de-ionized water (three extractions) to remove excess N-vinyl-2-caprolactam.

Example 32: Synthesis of Hemi-Aminal Ether of N-vinyl-2-caprolactam and 2-(dibutylamino)ethanol (DBAE)

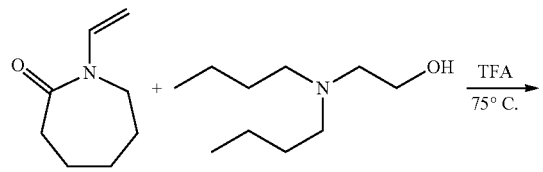

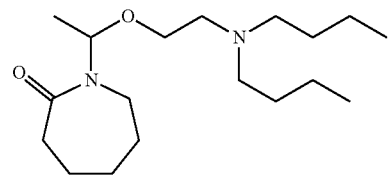

A quantity of 104.0 g of 2-(dibutylamino)ethanol (0.6 mol) was mixed with 36.1 g of acetic acid (0.6 mol) in a 250 mL beaker. Above mixture and 69.6 g of N-vinyl-2-caprolactam (0.50 mol) were charged into a 1-liter resin kettle, fitted with a propeller agitator, a heating mantle, a reflux condenser, and a thermocouple. The reactor was heated to 65° C. A quantity of 0.570 g of trifluoroacetic acid (TFA, 0.005 mol) was added into the reactor. After the initial exotherm, the reaction temperature was maintained at 75° C. for 6 hours. GC analysis was used to measure N-vinyl-2-caprolactam residual at 2 hrs, 4 hrs, and 6 hrs. At 6 hrs reaction time, the reaction mixture was cooled down to room temperature. The product was purified by washing with NaHCO₃ (one extraction) and de-ionized water (three extractions) to remove excess N-vinyl caprolactam.

Examples 33-38: Syntheses of N-alkenyl Cyclic Amide Aminals and Hemi-Aminal Ethers that do not have Polymerizable Groups For each of Examples 33-38, Example 32 is substantially repeated, substituting other N-alkenyl cyclic amides (first reactant) for N-vinyl-2-pyrrolidone and substituting other compounds having at least one hydroxyl and/or amino group (second reactant) for DBAE. Table 2 shows the structures of the first reactant, the second reactant and the corresponding aminal or hemi-aminal ether reaction product for each of the Examples 33-38.

One or more of the hydroxyl moiety may be replaced with a thiol moiety to yield the corresponding thioether product.

TABLE 2

Structures of reactants and product for Examples 33-38

| Example | First Reactant | Second Reactant | Reaction Product |
|---|---|---|---|
| 33 | ![vinyl pyrrolidone] | HO-CH₂CH₂-O-CH₂CH₂-O-CH₂CH₂-O-CH₂CH₂-OH | pyrrolidone-CH(CH₃)-O-CH₂CH₂-O-CH₂CH₂-O-CH₂CH₂-O-CH₂CH₂-OH |

TABLE 2-continued

Structures of reactants and product for Examples 33-38

| Example | First Reactant | Second Reactant | Reaction Product |
|---|---|---|---|
| 34 | vinyl pyrrolidone | HO-CH2CH2-O-CH2CH2CH2-O-CH2CH2CH2-OH | pyrrolidone-CH(CH3)-O-CH2CH2-O-CH2CH2CH2-O-CH2CH2CH2-OH |
| 35 | vinyl pyrrolidone | HO-CH2CH2CH2-O-CH2CH2CH2CH2-O-CH2CH2CH2-OH | pyrrolidone-CH(CH3)-O-...-O-...-O-CH(CH3)-pyrrolidone |
| 36 | vinyl caprolactam (7-membered) | HO-CH2CH2-O-CH2CH2-O-CH2CH2-OH | caprolactam-CH(CH3)-O-CH2CH2-O-CH2CH2-O-CH2CH2-NH2 |
| 37 | vinyl imidazolidinone | HO-CH2CH2CH2-O-CH2CH2CH2-OH | imidazolidinone-CH(CH3)-O-CH2CH2CH2-O-CH2CH2CH2-OH |
| 38 | vinyl imidazolidinone | HO-CH2CH2CH2-O-CH2CH2CH2-OH | imidazolidinone-CH(CH3)-O-...-O-CH(CH3)-imidazolidinone |

Example 39: Synthesis of Hemi-Aminal Ether of N-vinyl-2-pyrrolidone and Hydroxyethyl Cellulose A quantity of 43.1 g N-vinyl-2-pyrrolidone, 80.0 g hydroxyethylcellulose (HEC) (Cellosize™ 15, The Dow Chemical Company) and 100.0 g tetrahydrofuran (THF) were charged into a 1-L resin kettle, fitted with a propeller agitator, a heating mantle, a reflux condenser, and a thermocouple. The reactor was heated to 60° C. A quantity of 0.1 g trifluoroacetic acid (0.001 mol) was added into the reactor. After the initial exotherm, the reaction temperature was maintained at 60° C. for 24 hours. GC analysis was used to measure residual N-vinyl-2-caprolactam amounts after 2, 4, 6, 12, 18, and 24 hours. At t=24 hours, the reaction mixture was cooled to room temperature (about 22° C.), and remaining THF was removed using a rotary evaporator.

Example 40: Synthesis of Polymer of (A) N-vinyl-2-caprolactam and (B) Hemi-Aminal Ether of N-vinyl-2-caprolactam and 2-hydroxyethylmethacrylate

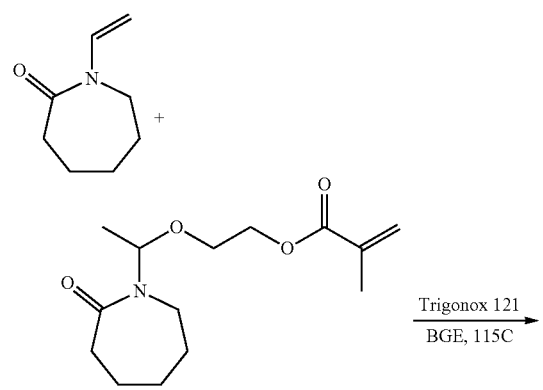

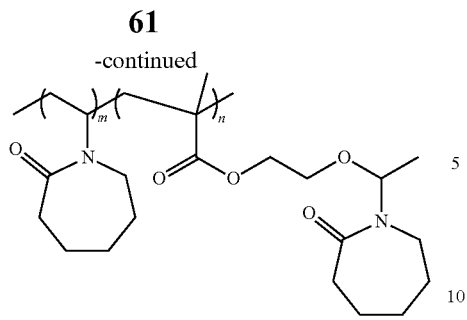

A monomer premix was prepared by mixing 15.0 g of the hemi-aminal ether of N-vinyl-2-caprolactam and 2-hydroxyethyl methacrylate (product of Example 10), 135.0 g N-vinyl-2-caprolactam, 25.0 g 2-butoxyethanol, and 6.0 g t-amylperoxy-2-ethylhexanoate (Trigonox® 121, Akzo Nobel N.V.). The monomer premix was pH adjusted to 10.0 using 1N NaOH solution and stored in an ice bath. A quantity of 200.0 g BGE was charged into a 1-L resin kettle, fitted with a propeller agitator, a heating mantle, a reflux condenser, nitrogen gas inlet and outlet tubes, and a thermocouple. The reactor was purged with nitrogen gas, then heated to 115° C. The time was set to 0 when the reactor temperature stabilized at 115° C., and at this time the monomer premix was metered into the reactor in 3 hours through a Masterflex pump. When the monomer premix addition was complete (time=3 hours), the reactor temperature was cooled to 106° C. over the period of half an hour (time=3.5 hours). At 3.5 hours, 4.0 hours, and 4.5 hours, three portions of Trigonox® 121, each of 0.5 g, were added into the reactor at half hour reaction intervals. The reactor temperature was held at 106° C. for an additional half hour. At time=5.0 hours, the reactor content was cooled down to room temperature and discharged.

We claim:

1. A homopolymer obtained by polymerizing a monomer obtained by reaction of at least:

(A) at least one first reactant represented by a structure

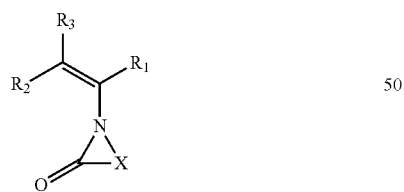

wherein X is a functionalized or unfunctionalized $C_1$-$C_5$ alkylene group optionally having one or more heteroatoms, and each $R_1$, $R_2$ and $R_3$ is independently selected from the group consisting of hydrogen and functionalized and unfunctionalized alkyl groups optionally having one or more heteroatoms, and (B) at least one second reactant having at least one hydroxyl moiety or thiol moiety, and at least one polymerizable moiety.

2. The homopolymer according to claim 1 wherein said monomer is selected from the group consisting of:

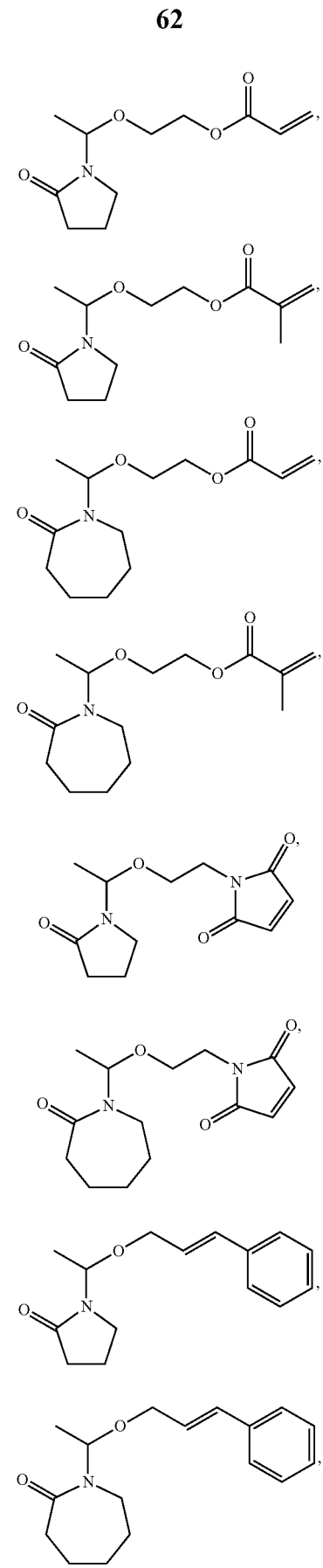

-continued
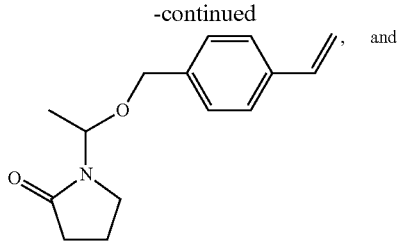, and
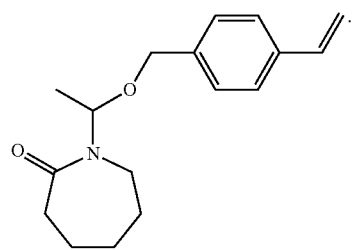.
* * * * *